United States Patent
Kahn et al.

(10) Patent No.: US 8,506,779 B2
(45) Date of Patent: *Aug. 13, 2013

(54) ELECTROCHEMICAL SENSORS

(75) Inventors: Carolyn R. Kahn, San Francisco, CA (US); Elicia Wong, Sydney (AU); Vern Norviel, San Jose, CA (US)

(73) Assignee: Sensor Innovations, Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/241,171

(22) Filed: Sep. 22, 2011

(65) Prior Publication Data

US 2012/0067724 A1 Mar. 22, 2012

Related U.S. Application Data

(63) Continuation of application No. 12/049,230, filed on Mar. 14, 2008.

(60) Provisional application No. 60/942,646, filed on Jun. 7, 2007, provisional application No. 60/942,644, filed on Jun. 7, 2007, provisional application No. 60/942,641, filed on Jun. 7, 2007, provisional application No. 60/949,805, filed on Jul. 13, 2007.

(51) Int. Cl.
*G01N 27/26* (2006.01)

(52) U.S. Cl.
USPC .......... 204/416; 204/415; 204/400; 548/406; 324/438

(58) Field of Classification Search
USPC .......... 204/400–436; 205/775–792; 548/406
See application file for complete search history.

(56) References Cited

U.S. PATENT DOCUMENTS

| | | | |
|---|---|---|---|
| 3,682,160 A | * | 8/1972 | Murata .................. 600/302 |
| 3,926,764 A | | 12/1975 | Ruzicka et al. |
| 3,982,960 A | | 9/1976 | Hoekje et al. |
| 4,592,807 A | | 6/1986 | Switzer |
| 4,628,013 A | | 12/1986 | Figard et al. |

(Continued)

FOREIGN PATENT DOCUMENTS

| DE | 10062044 A1 | 6/2002 |
|---|---|---|
| DE | 10108539 A1 | 9/2002 |

(Continued)

OTHER PUBLICATIONS

Bruns (Are meters accurate enough, Diabetes Forecast, Apr. 2008).*

(Continued)

*Primary Examiner* — J. Christopher Ball
*Assistant Examiner* — Jennifer Dieterle
(74) *Attorney, Agent, or Firm* — Wilson Sonsini Goodrich & Rosati

(57) ABSTRACT

Described herein are substrates, sensors and systems related to measuring the concentration of an analyte such as hydrogen ion in a sample. Redox active moieties whose reduction and/or oxidation potentials are sensitive to the presence of an analyte are immobilized onto a surface of an electrode. Immobilized redox active moieties whose reduction and/or oxidation potential are insensitive to the analyte can be used for reference. Voltammetric measurements made using such modified surfaces can accurately determine the presence and/or concentrations of analytes in a sample of interest. The electrochemical sensors of the invention are robust and can be made so as not to require calibration or recalibration.

30 Claims, 18 Drawing Sheets

(56) References Cited

U.S. PATENT DOCUMENTS

| | | | |
|---|---|---|---|
| 4,704,193 A | 11/1987 | Bowers et al. | |
| 4,752,398 A | 6/1988 | Holbein et al. | |
| 4,758,325 A | 7/1988 | Kanno et al. | |
| 4,900,424 A | 2/1990 | Birth et al. | |
| 4,914,046 A | 4/1990 | Tobin et al. | |
| 5,017,540 A | 5/1991 | Sandoval et al. | |
| 5,120,421 A | 6/1992 | Glass et al. | |
| 5,139,626 A | 8/1992 | Yamaguchi et al. | |
| 5,223,117 A * | 6/1993 | Wrighton et al. | 204/415 |
| 5,296,125 A | 3/1994 | Glass et al. | |
| 5,326,738 A | 7/1994 | Sandoval et al. | |
| 5,331,966 A | 7/1994 | Bennett et al. | |
| 5,364,797 A | 11/1994 | Olson et al. | |
| 5,403,462 A | 4/1995 | Lev et al. | |
| 5,503,728 A | 4/1996 | Kaneko et al. | |
| 5,525,511 A | 6/1996 | D'Costa | |
| 5,534,132 A | 7/1996 | Vreeke et al. | |
| 5,540,828 A | 7/1996 | Yacynych | |
| 5,557,596 A | 9/1996 | Gibson et al. | |
| 5,567,302 A * | 10/1996 | Song et al. | 205/777.5 |
| 5,676,820 A | 10/1997 | Wang et al. | |
| 5,770,453 A | 6/1998 | Beer et al. | |
| 5,786,604 A | 7/1998 | Yamashita et al. | |
| 5,866,434 A | 2/1999 | Massey et al. | |
| 6,042,788 A | 3/2000 | De Wit et al. | |
| 6,096,497 A | 8/2000 | Bauer | |
| 6,175,752 B1 | 1/2001 | Say et al. | |
| 6,221,586 B1 | 4/2001 | Barton et al. | |
| 6,224,745 B1 | 5/2001 | Baltruschat | |
| 6,262,941 B1 | 7/2001 | Naville | |
| 6,322,963 B1 | 11/2001 | Bauer | |
| 6,340,588 B1 | 1/2002 | Nova et al. | |
| 6,342,347 B1 | 1/2002 | Bauer | |
| 6,359,444 B1 | 3/2002 | Grimes | |
| 6,376,977 B1 | 4/2002 | Kawai et al. | |
| 6,391,471 B1 | 5/2002 | Hiraoka et al. | |
| 6,416,651 B1 | 7/2002 | Millar | |
| 6,444,326 B1 | 9/2002 | Smith | |
| 6,461,820 B1 | 10/2002 | Barton et al. | |
| 6,498,492 B1 | 12/2002 | Rezvani | |
| 6,503,701 B1 | 1/2003 | Bauer | |
| 6,562,210 B1 * | 5/2003 | Bhullar et al. | 204/403.03 |
| 6,620,315 B2 | 9/2003 | Martin | |
| 6,649,350 B2 | 11/2003 | Barton et al. | |
| 6,690,182 B2 | 2/2004 | Kelly et al. | |
| 6,738,670 B1 | 5/2004 | Almendinger et al. | |
| 6,770,190 B1 | 8/2004 | Milanovski et al. | |
| 6,929,636 B1 | 8/2005 | von Alten | |
| 7,038,470 B1 | 5/2006 | Johnson | |
| 7,045,054 B1 | 5/2006 | Buck et al. | |
| 7,109,271 B2 | 9/2006 | Liu et al. | |
| 7,160,678 B1 | 1/2007 | Kayyem et al. | |
| 7,202,037 B2 | 4/2007 | Barton et al. | |
| 7,399,400 B2 | 7/2008 | Soundarrajan | |
| 7,429,630 B2 | 9/2008 | Liu et al. | |
| 7,592,151 B2 | 9/2009 | Liu et al. | |
| 7,635,423 B2 | 12/2009 | Boussaad et al. | |
| 7,731,835 B2 | 6/2010 | Buck et al. | |
| 7,775,083 B2 | 8/2010 | Potyrailo et al. | |
| 7,833,805 B2 | 11/2010 | Cuppoletti | |
| 7,901,555 B2 | 3/2011 | Jiang et al. | |
| 7,947,405 B2 | 5/2011 | Mittelsteadt et al. | |
| 2001/0016682 A1 | 8/2001 | Berner et al. | |
| 2002/0015963 A1 | 2/2002 | Keen | |
| 2002/0019707 A1 * | 2/2002 | Cohen et al. | 702/30 |
| 2002/0052076 A1 | 5/2002 | Khan et al. | |
| 2002/0090632 A1 | 7/2002 | Buck et al. | |
| 2002/0090738 A1 * | 7/2002 | Cozzette et al. | 436/518 |
| 2002/0116042 A1 | 8/2002 | Boling | |
| 2003/0081463 A1 * | 5/2003 | Bocian et al. | 365/200 |
| 2003/0148169 A1 * | 8/2003 | Willner et al. | 429/43 |
| 2003/0153900 A1 * | 8/2003 | Aceti et al. | 604/890.1 |
| 2003/0206026 A1 | 11/2003 | Diakonov et al. | |
| 2004/0134798 A1 * | 7/2004 | Toumazou et al. | 205/793.5 |
| 2004/0138840 A1 | 7/2004 | Wolfe | |
| 2005/0029125 A1 | 2/2005 | Jiang et al. | |
| 2005/0097941 A1 | 5/2005 | Sandvik et al. | |
| 2005/0110053 A1 * | 5/2005 | Shur et al. | 257/253 |
| 2005/0186333 A1 | 8/2005 | Douglas | |
| 2005/0270822 A1 | 12/2005 | Shrivastava et al. | |
| 2006/0151324 A1 * | 7/2006 | Davies et al. | 204/484 |
| 2007/0034530 A1 | 2/2007 | Lin et al. | |
| 2007/0272552 A1 | 11/2007 | Jiang et al. | |
| 2008/0023328 A1 | 1/2008 | Jiang et al. | |
| 2008/0035481 A1 | 2/2008 | McCormack et al. | |
| 2008/0190855 A1 | 8/2008 | Compton et al. | |
| 2008/0302660 A1 | 12/2008 | Kahn et al. | |
| 2009/0014329 A1 | 1/2009 | Silveri | |
| 2009/0178921 A1 | 7/2009 | Lawrence et al. | |
| 2009/0218239 A1 | 9/2009 | Gooding et al. | |
| 2010/0133547 A1 | 6/2010 | Kunze et al. | |
| 2010/0179399 A1 | 7/2010 | Goode, Jr. et al. | |

FOREIGN PATENT DOCUMENTS

| | | |
|---|---|---|
| EP | 0228969 A2 | 7/1987 |
| EP | 0228969 A3 | 3/1989 |
| EP | 0411127 A1 | 2/1991 |
| EP | 1621636 B1 | 1/2010 |
| GB | 2347746 A | 9/2000 |
| GB | 2430749 A | 4/2007 |
| GB | 2450002 B | 4/2009 |
| GB | 2451596 B | 9/2009 |
| JP | 64-41852 | 2/1989 |
| JP | 2005-257684 A | 9/2005 |
| WO | WO 98/57159 A1 | 12/1998 |
| WO | WO 00/11474 A1 | 3/2000 |
| WO | WO 02/48701 A2 | 6/2002 |
| WO | WO 02/060812 A2 | 8/2002 |
| WO | WO 02/060812 A3 | 11/2002 |
| WO | WO 02/48701 A3 | 4/2003 |
| WO | WO 03/058692 A1 | 7/2003 |
| WO | WO 2005/066618 A1 | 7/2005 |
| WO | WO2005066618 * | 7/2005 |
| WO | WO 2005/074161 A1 | 8/2005 |
| WO | WO 2005/085825 A1 | 9/2005 |
| WO | WO 2006/007533 A1 | 1/2006 |
| WO | WO 2006/120396 A2 | 6/2006 |
| WO | WO 2006/120396 A3 | 2/2007 |
| WO | WO 2007/017252 A1 | 2/2007 |
| WO | WO 2007/034131 A1 | 3/2007 |
| WO | WO 2007/106936 A1 | 9/2007 |
| WO | WO 2007/139574 A1 | 12/2007 |
| WO | WO 2008/154409 A1 | 12/2008 |
| WO | WO 2009/009448 A1 | 1/2009 |
| WO | WO 2009/115840 A1 | 9/2009 |
| WO | WO 2010/104962 A1 | 9/2010 |
| WO | WO 2010/111531 A2 | 9/2010 |
| WO | WO 2010/118156 A1 | 10/2010 |
| WO | WO 2010/111531 A3 | 1/2011 |

OTHER PUBLICATIONS

Lim, et al. Synthesis, charaterization and catalytic performance of porous nafion resin/silica nanocomposites for esterification of lauric acid and methanol. Journal of Physical Science. 2009; 20(2):23-36.
Liu, et al. Nafion/PTFE composite membranes for fuel cell applications. Journal of Membrane Science. 2003; 212:213-223.
U.S. Appl. No. 13/329,135, filed Dec. 16, 2011, Kahn et al.
Bateman, et al. Alkylation of Porous Silicon by Direct Reaction with Alkenes and Alkynes. Angew. Chem. Int. Ed. 1998; 37(19): 2683-2685.
Bergveld. ISFET, Theory and Practice. IEEE Sensor Conference, Toronto, Oct. 2003, 1-26.
Buriak. Organometallic Chemistry on Silicon and Germanium Surfaces. Chem. Review. 2002; 102(5):1271-1308.
Buriak. Organometallic Chemistry on Silicon Surfaces: formation of functional monolayers bound through Si-C bonds. Chem. Commun. 1999; 1051-1060.
Carroll, et al. Low-Temperature Preparation of Oxygen—and Carbon-Free Silicon and Silicon-Germanium Surfaces for Silicon and Silicon—Germanium Epitaxial Growth by Rapid Thermal Chemical Vapor Deposition. J. Electrochem Soc. 2000; 147(12):4652-4659.

Casimiri, et al. Co-immobilized L-lactate oxidase and L-lactate dehydrogenase on a film mounted on oxygen electrode for highly sensitive L-lactate determination. Biosensors and Bioelectronics. 1996; 11(8):783-789.

Chou, et al. Study on the temperature effects of Al2O3 gate pH-ISFET. Sensors and Actuators B. Elsevier Sequoia S.A. Lausanne, CH. 2002; 81(2-3):152-157.

Delamar, et al. Modification of carbon fiber surfaces by electrochemical reduction to carbon epoxy composites. Carbon, Elsevier, Oxford, BG. 1997; 35(6):801-807.

Evans, R. A. The Rise of Azide—Alkyne 1,3-Dipolar 'Click' Cycloaddition and its Application to Polymer Science and Surface Modification. Australian Journal of Chemistry. 2007; 60(6) 384-395.

Fischer, et al. Derivatization of surfaces via reaction of strained silicon-carbon bonds. Characterization by photoacoustic spectroscopy. American Chemical Society. 1979; 101(22):6501-6506.

Gee, et al. Infrared spectroscopy of hydrogen-terminated gallium arsenide (100). J. Vacuum Sci. Tech. Jul./Aug. 1992; 10(4):892-896.

Hammond, et al. Synthesis N.M.R. spectra and structure of macrocyclic compounds containing Ferrocene unit. J. Chem. Soc. Perkin. Trans. 1983; I 707-715.

Heald, et al. Chemical Derivatisation of Multiwalled Carbon Nanotubes Using Diazonium Salts. Chemphyschem. Nov. 12, 2004; 5(11):1794-9.

International search report dated Sep. 11, 2008 for PCT Application No. US2008/066165.

Johnson, et al. Poly(L-cysteine) as an electrochemically modifiable ligand for trace metal chelation. Analytical chemistry. 2005; 77(1):30-35.

Kolb, et al. Click Chemistry: Diverse Chemical Function from a Few Good Reactions. Angew Chem Int Ed Engl. Jun. 1, 2001;40(11):2004-2021.

Kwon, et al. An electrochemical immunosensor using ferrocenyl-tethered dendrimer. Analyst. Mar. 2006;131(3):402-6.

Lafitte, et al. Anthraquinone-ferrocene film electrodes: Utility in pH and oxygen sensing. Electrochemistry Communications. 2008; 10(12):1831-1834.

Lawrence, et al. Triple Component Carbon Epoxy pH Probe. Electroanalysis. 2007; 19(4):424-428.

Leventis, et al. Derivatised carbon powder electrodes: reagentless pH sensors. Talanta. 2004; 63(4):1039-1051.

Maoz, et al. On the formation and structure of self-assembling monolayers. I: Comparative ATR-wettability study of Langmuir-Blodgett and adsorbed films on flat substrates and glass microbeads. Journal of colloid and interface science. 1984; 100(2):465-496.

Medina, et al. Ferrocenyldimethyl-[2.2]-cryptand: Solid State Structure of the External Hydrate and Al¬kali and Alkaline-earth-dependent Electrochemical Behaviour. J. Chem. Soc. Chem. Commun. 1991;290-292.

Pandurangappa, et al. Homogeneous Chemical Derivatisation of Carbon Particles: A Novel Method for Functionalizing Carbon Surfaces. The Analyst. 2002; 127:1568-1571.

Pandurangappa, et al. Physical adsorption of N,N'-diphenyl-p-phenylenediamine onto carbon particles: application to the detection of sulfide. Analyst. May 2003;128(5):473-9.

Robinson, et al. Redox-sensitive copolymer: a single-component pH sensor. Anal Chem. Apr. 1, 2006;78(7):2450-5.

Robinson, et al. Vinylferrocene homopolymer and copolymers: an electrochemical comparison. Anal Sci. Mar. 2008;24(3):339-43.

Schmuki, et al. In situ characterization of anodic silicon oxide films by ac impedance measurements. Electrochem. Soc. 1995; 142(5):1705-1712.

Seymour, et al. Reaction with N,N-Diethyl-p-phenylenediamine: A Procedure for the Sensitive Square-Wave Voltammetric Detection of Chlorine. Electroanalysis. 2003; 15(8):689-694.

Shu, et al. Synthesis and Charge-Transport Properties of Polymers Derived from the Oxidation of 1-Hydro-1-'46-(pyrrol-1-yphexyl)-4,4'-bipyridinium Bis(hexa¬fluorophosphate) and Demonstration of a pH-Sensitive Microelectrochemical Transistor Derived from the Redox Properties of a Conventional Redox Center. J. Phys. Chem. 1988; 92: 5221-5229.

Spetz et al. Current status of silicon carbide based high-temperature gas sensors. IEEE Transactions on Electron Devices. IEEE Service Center, Pisacataway, NJ, US. Mar. 1999; 46(3): p. 561, XP011016819.

Stewart, et al. Direct Covalent Grafting of Conjugated Molecules onto Si, GaAs, and Pd Surfaces from Aryldiazonium Salts. J. Am. Chem. Soc. 2004; 126:370-378.

Streeter, et al. A sensitive reagentless pH probe with a ca. 120 mV/pH unit response. Journal of Solid State Electrochemistry. 2004; 8(10):718-721.

Sun, et al. Optimized cleaning method for producing device quality InP(100) surfaces J. Appl. Phys. 2005; 97:124902. doi:10.1063/1.1935745.

UK search report dated Jun. 24, 2008 for GB application No. 0810556.1.

Wildgoose, et al. Abrasively Immobilised Multiwalled Carbon Nanotube Agglomerates: A Novel Electrode Material Approach for the Analytical Sensing of pH ChemPhysChem. 2004; 5:669-677. vol. 5, Issue 5, pp. 669-677, May 17, 2004.

Wildgoose, et al. Anthraquinone-derivatised carbon powder: reagentless voltammetric pH electrodes. Talanta. 2003; 60:887-893.

Wildgoose, et al. Graphite powder and multiwalled carbon nanotubes chemically modified with 4-nitrobenzylamine. Chemphyschem. Feb. 2005;6(2):352-62.

Yu, et al. Electron-transfer Characteristics of Ferrocene Attached to Single-walled Carbon Nanotubes (SWCNT) Arrays directly anchored to silicon (100). Electrochimica Acta. 2007; 52: 6206-6211.

Shinwari, et al. Microfabricated reference electrodes and their biosensing applications. Sensors. 2010; 10:1679-1715.

Dicks, et al. The application of ferrocene-modified n-type silicon in glucose biosensors. Electroanalysis. Jan. 1993; 5(1):1-9.

International search report and written report dated Nov. 23, 2012 for PCT Application No. US2011/065652.

U.S. Appl. No. 13/787,300, filed Mar. 6, 2013, Kahn et al.

U.S. Appl. No. 13/787,534, filed Mar. 6, 2013, Kahn et al.

Ghica, et al. Development of a carbon film electrode ferrocene-mediated glucose biosensor. Analytical letters. 2005; 38(6):907-920.

Office action dated May 20, 2013 for U.S. Appl. No. 13/329,135.

Sigma Aldrich Spec Sheet, downloaded May 16, 2013.

Ward, et al. A new amperometric glucose microsensor: in vitro and short-term in vivo evaluation. Biosens Bioelectron. 2002 Mar;17(3):181-9.

* cited by examiner

US 8,506,779 B2

ELECTROCHEMICAL SENSORS

CROSS-REFERENCE

This application is a continuation patent application of U.S. patent application Ser. No. 12/049,230, filed Mar. 14, 2008, which claims the benefit of U.S. Provisional Patent Application No. 60/942,646, filed Jun. 7, 2007, U.S. Provisional Patent Application No. 60/942,644, filed Jun. 7, 2007, U.S. Provisional Patent Application No. 60/942,641, filed Jun. 7, 2007, and U.S. Provisional Patent Application No. 60/949,805, filed Jul. 13, 2007, all of which applications are incorporated herein by reference in their entirety.

BACKGROUND OF THE INVENTION

The measurement of analyte concentration, in particular, hydrogen ion concentration or pH is important in a number of research, industrial, and manufacturing processes. For instance, the monitoring of pH is routinely practiced in food and beverage, biofuel, biopharmaceuticals, as well as in the treatment of water and waste.

Many conventional pH sensors use a potentiometric approach which involves the use of glass electrode to measure pH. The potentiometric approach suffers from several profound drawbacks. One limitation of potentiometric sensors is the need for constant calibration. Potentiometric pH electrodes, like batteries, tend to run down with time and use. As the potentiometric electrode ages, its glass membrane tends to change in resistance, which in turn will alter the electrode potential. For this reason, the glass electrodes require calibration on a regular basis. The need for constant recalibration to provide an accurate pH output has significantly impedes industrial applications especially where constant in-line pH measurements are required. Recalibration is particularly cumbersome in a biotech environment where pH measurement is conducted in medium containing biological materials. Another significant drawback of conventional pH sensors is that the glass electrodes have internal solutions, which in some cases can leak out into the solution being measured. The glass electrodes can also become clogged by species in the measuring solution, e.g. proteins, causing the glass electrode to foul.

Thus, there remains a considerable need for reliable and consistent analyte sensors, and in particular, pH sensors.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE INVENTION

In one aspect, the invention comprises a silicon substrate having a silicon surface, wherein the surface comprises a redox-active moiety immobilized thereon, said redox-active moiety exhibiting an oxidation potential and/or a reduction potential that is sensitive to the presence of an analyte. In some embodiments, immobilized thereon is also a second redox-active moiety having an oxidation potential and/or a reduction potential that is substantially insensitive to the presence of the analyte. In some embodiments the analyte is an ion. In some embodiments the analyte is hydrogen ion. In some embodiments, the silicon substrate comprises porous silicon, for example with the average pore size ranges from about 1 nm to about 500 nm. In some embodiments, the porosity of the porous silicon is between about 1% and about 98%. In some embodiments, the silicon substrate comprises unpolished silicon. In some embodiments, the silicon substrate comprises polished silicon.

In some embodiments, the redox-active moiety is directly bound to the surface. In some embodiments the redox-active moiety is covalently bound to the surface. In some embodiments the redox-active moiety is covalently bound to the surface through a linker. In some embodiments the redox-active moiety is covalently bound to a polymer that is immobilized onto the surface of the silicon substrate. In some embodiments the redox-active moiety is covalently bound to a polymer that is covalently bound to the surface of the silicon substrate In some embodiments the silicon is doped. In some embodiments the silicon is n-doped. In some embodiments the silicon is p-doped. In some embodiments the substrate is crystalline silicon wherein the surface displaying predominantly one crystalline plane.

In some embodiments the substrate has a plurality of zones wherein each zone comprises a redox-active moiety immobilized thereon, said redox-active moiety exhibiting an oxidation potential and/or a reduction potential that is sensitive to the presence of an analyte. In some embodiments a first zone comprises a redox moiety sensitive to a first analyte, and a second zone comprises a redox moiety sensitive to a second analyte. Some embodiments further comprise a third redox-active moiety exhibiting an oxidation potential and/or a reduction potential that is sensitive to the presence of a second analyte. In some embodiments the second analyte is ammonia, oxygen or carbon dioxide.

Another aspect of the invention is a sensor for detecting the presence of an analyte comprising: a silicon electrode having a silicon surface having immobilized thereon a redox-active moiety, wherein the redox-active moiety exhibits an oxidation potential and/or a reduction potential that is sensitive to the presence of said analyte. In some embodiments the analyte is hydrogen ion and the redox-active moiety is sensitive to hydrogen ion concentration. In some embodiments the sensor comprises a plurality of redox-active moieties, wherein at least one of the redox-active moieties is sensitive to the presence of an analyte, and at least one other redox-active moiety is substantially insensitive to the presence of said analyte. In some embodiments the moiety that is substantially insensitive to the presence of hydrogen ion has a substituent selected from the group consisting of ferrocene, polyvinylferrocene, viologen, polyviologen, and polythiophene. In some embodiments the moiety that is substantially insensitive to the presence of hydrogen ion is ferrocene or a derivative of ferrocene.

In some embodiments the redox-active moiety that is sensitive to the presence of the hydrogen ion comprises a substituent selected from the group consisting of anthracenes, quinones, anthroquinones, phenanthroquinones, phenylene diamines, catechols, phenothiazinium dyes, monoquaternized N-alkyl-4,4'-bipyridinium, RuOx, and Ni(OH)2. In some embodiments the redox-active moiety that is sensitive to the presence of hydrogen ion comprises a substituent comprising anthracene. In some embodiments the redox-active moiety that is sensitive to the presence of hydrogen ion comprises a substituent comprising an anthraquinone or a phenanthraquinone. In some embodiments the redox-active moiety that is sensitive to the presence of an analyte is sensitive to the concentration of the analyte. In some embodiments the oxidation potential and/or reduction potential of the redox-active moiety is sensitive to the concentration of the analyte in a range from about $10^{-3}$ M to about $10^{-10}$ M. In some embodiments the oxidation potential and/or reduction potential of the redox-active moiety is sensitive to the concentration of the analyte in a range from about $10^{-2}$ M to about $10^{-13}$ M. In some embodiments the sensor detects hydrogen ion concentration from about pH3 to about pH10. In some embodiments sensor detects hydrogen ion concentration from about pH2 to about pH13. In some embodiments the sensor measures hydrogen ion concentration within an accuracy of about plus or minus 0.1 pH unit. In some embodiments the sensor measures hydrogen ion concentration within an accuracy of about plus or minus 0.01 pH units.

In some embodiments the redox-active moiety is covalently bound to the surface of the electrode. In some embodiments the redox-active moiety is bound to a polymer that is immobilized onto the surface of the electrode.

In some embodiments the silicon electrode is doped. In some embodiments the silicon electrode is p-doped. In some embodiments the silicon electrode is doped with boron. In some embodiments the silicon electrode is n-doped. In some embodiments the silicon electrode is doped with phosphorous.

In some embodiments the electrode comprises a monolithic piece of silicon. In some embodiments the silicon electrode comprises a composite electrode, said composite electrode comprising silicon particles in a matrix. In some embodiments the silicon electrode comprises a composite electrode bound to a conductive substrate. In some embodiments the silicon particles are present in an amount such that a conductive path is created across the composite electrode.

In some embodiments the electrode comprises porous silicon. In some embodiments the electrode comprises unpolished silicon. In some embodiments the electrode comprises polished silicon.

In some embodiments the silicon electrode has a resistivity within the range of about 0.01 to about 1000 $\Omega$-cm. In some embodiments the silicon electrode has a resistivity within the range of about 1 to about 100 $\Omega$-cm.

In some embodiments the sensor is capable of measuring analyte concentration without calibration with an external standard. In some embodiments the sensor remains sensitive to the analyte without calibration after a first use by an end user.

In some embodiments the analyte is hydrogen ion and the sensor remains sensitive to hydrogen ion after exposure to a cell culture medium for at least about 6 days. In some embodiments the sensor is capable of measuring pH with an accuracy of about plus or minus 0.2 units after exposure to the cell culture medium for at least about 6 days. In some embodiments the analyte is hydrogen ion and the sensor is capable of measuring pH with an accuracy of about plus or minus 0.2 units after autoclave treatment at 121° C. for 40 minutes. In some embodiments the sensor is capable of measuring pH with an accuracy of about plus or minus 0.2 units after autoclave treatment at 121° C. for 400 minutes.

One aspect of the invention is a method for forming an analyte-sensitive silicon electrode, said electrode having a silicon surface, the method comprising: immobilizing a redox-active moiety that is sensitive to the presence of an analyte onto the silicon surface. In some embodiments immobilizing the redox-active moiety covalently binds the redox-active moiety to the surface. In some embodiments the redox-active moiety is covalently bound to the surface through a linker. In some embodiments the redox-active moiety comprises hydrosilation, a free radical reaction, carbodiimide coupling, a Diels-Alder reaction, a Michael addition, or click chemistry. In some embodiments the redox-active moiety is covalently bound to a polymer that is immobilized onto the surface. In some embodiments the step of immobilizing comprises polymerization including a monomer or oligomer comprising a redox-active moiety.

In some embodiments the polymerization of a monomer or oligomer comprising a redox-active moiety includes a reaction with a functional group covalently bound to the silicon surface, whereby the polymer formed by polymerization is covalently bound to the silicon surface. In some embodiments the monomer or oligomer is electropolymerized onto the silicon surface. In some embodiments the step of immobilizing comprises coating or casting the polymer onto the surface.

In some embodiments the silicon surface comprises a composite electrode that comprises silicon particles within a matrix. In some embodiments, prior to immobilizing the redox-active moiety, the silicon surface is rendered porous.

One aspect of the invention is a method of forming a silicon surface derivatized with one or more redox-active moieties comprising: contacting an H-terminated silicon surface with the one or more redox-active moieties wherein at least one redox active moiety is sensitive to the presence of an analyte, and wherein each redox-active moiety comprises a functional group that will react with the H-terminated silicon surface to form a covalently bond, thereby forming a derivatized silicon surface. In some embodiments the surface comprises at least two redox active moieties and one of the redox active moieties is insensitive to the presence of the analyte. In some embodiments the H-terminated silicon surface is formed by treatment with hydrofluoric acid. In some embodiments the functional group is a vinyl group. In some embodiments the functional group is an aldehyde group.

One aspect of the invention is a method of determining the concentration of an analyte, comprising: (a) placing an electrode in contact with said analyte, said electrode comprising a silicon substrate with silicon surface having immobilized thereon an analyte-sensitive redox-active moiety, said analyte-sensitive redox-active moiety exhibiting an oxidation potential and/or reduction potential that is sensitive to the concentration of the analyte; (b) applying a plurality of potentials to the electrode; and (c) measuring the current through the electrode at the plurality of potentials to determine a reduction and/or oxidation potential of the analyte-sensitive redox-active moiety, thereby determining the concentration of the analyte.

In some embodiments the measuring of the current at the plurality of potentials provides a peak current, and whereby the peak current is used to determine reduction and/or oxidation potential of the analyte-sensitive redox-active moiety. In some embodiments the analyte is hydrogen ion. In some embodiments the electrode further comprises an analyte-insensitive redox-active moiety having a reduction and/or oxidation potential that is substantially insensitive to the analyte, further comprising determining the oxidation and/or reduction potential of the analyte-insensitive redox-active moiety, and determining the concentration of the analyte from the difference in the oxidation and/or reduction potentials of the analyte-sensitive and analyte-insensitive moieties. In some embodiments the analyte is provided in a solution.

One aspect of the invention is an analyte-sensing system comprising: a working electrode having a silicon surface that has immobilized thereon a redox-active moiety, wherein the redox-active moiety has an oxidation potential and/or reduction potential that is sensitive to the presence of said analyte; a counter electrode and optionally a reference electrode; a source for supplying a plurality of potentials to the working electrode; and a device for measuring current through the working electrode at the plurality of potentials.

In some embodiments the silicon surface also has immobilized thereon a second redox-active moiety having an oxidation potential and/or reduction potential that is insensitive to the presence of said analyte. In some embodiments the source for supplying a plurality of potentials is a potentiostat capable of applying square waves for square wave voltammetry.

Some embodiments further comprise a computation system that communicates with the device for measuring current, having algorithms for calculating reduction or oxidation potential from the measured current at a plurality of potentials.

In some embodiments the system is used as an in-line sensor in a process.

In some embodiments the currents measured at a plurality of potentials are used to determine analyte concentration, and the determined analyte concentration is used to control a process parameter.

One aspect of the invention is a method comprising: measuring a pH value of a step in a water or waste treatment process with a voltammetric pH sensor, wherein the pH sensor comprises a redox-active moiety that is sensitive to hydrogen ion concentration, and a redox-active moiety that is substantially insensitive to hydrogen ion; and using the pH value to monitor or control the treatment process.

One aspect of the invention is a method comprising: measuring a pH value of a reaction mixture in an biopharmaceutical process with a voltammetric pH sensor, wherein the pH sensor comprises a redox-active moiety that is sensitive to hydrogen ion concentration, and a redox-active moiety that is substantially insensitive to hydrogen ion concentration to obtain a pH value; and using the pH value to monitor the biopharmaceutical process. In some embodiments the pH value is measured on a sample obtained from the reaction mixture.

One aspect of the invention is a reactor for carrying out a biopharmaceutical process wherein the reactor comprises a pH sensor having a redox-active moiety that is sensitive to hydrogen ion concentration, and a redox-active moiety that is substantially insensitive to hydrogen ion concentration.

In some embodiments the pH sensor is a voltammetric pH sensor. In some embodiments the reactor is a disposable bioreactor. In some embodiments the reactor is a bioprocess flexible container.

Another aspect of the invention is a method for carrying out an industrial process comprising: measuring a pH value of a step of an industrial process with a voltammetric pH sensor having a redox-active moiety that is sensitive to hydrogen ion concentration, and a redox-active moiety that is substantially insensitive to hydrogen ion concentration; and using the pH value to carry out the industrial process.

Another aspect of the invention is a sensor for measuring ion concentration in a bodily fluid within a body comprising: an electrode configured to be in contact with a bodily fluid, said electrode comprising a silicon surface that has immobilized thereon a redox-active moiety, wherein the redox-active moiety has an oxidation potential and/or reduction potential that is sensitive to concentration of said ion.

One aspect of the invention is a method of measuring concentration in a bodily fluid within a body comprising: placing in contact with the bodily fluid; and operating the sensor to yield a value of the concentration of the ion present in said bodily fluid.

One aspect of the invention is a bioreactor comprising a reservoir for containing a reaction mixture and a pH probe wherein the pH probe comprises an electrode having a silicon surface, the silicon surface having immobilized thereon a redox active moiety having a reduction and/or oxidation potential that is sensitive to the presence of hydrogen ion.

In some embodiments the probe further comprises a silicon surface having immobilized thereon a redox active moiety having a reduction and/or oxidation potential that is insensitive to the presence of hydrogen ion. In some embodiments the silicon surface on which the redox active moiety having a reduction and/or oxidation potential that is sensitive to the presence of hydrogen ion is immobilized is the same silicon surface on which the redox active moiety having a reduction and/or oxidation potential that is insensitive to the presence of hydrogen ion is immobilized on. In some embodiments the probe further comprises a counter electrode.

DESCRIPTION OF THE INVENTION

Figure 1:
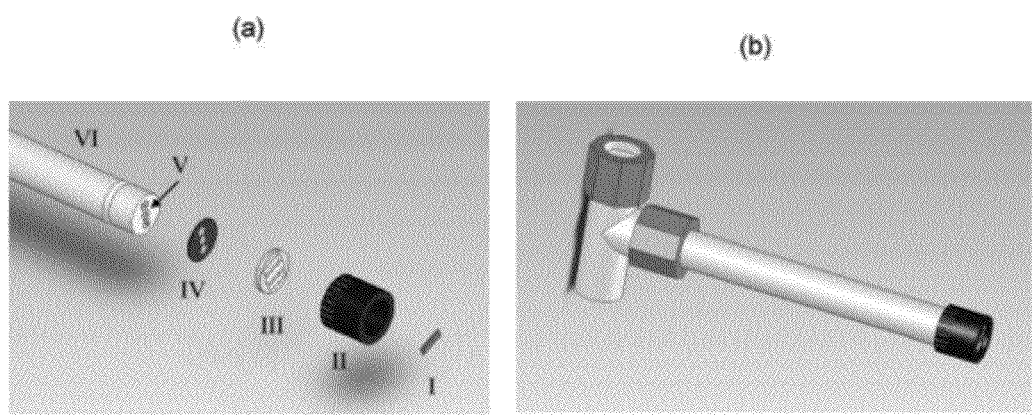
FIG. 1(a) shows a blow up drawing illustrating an embodiment of the invention comprising a silicon electrode sensor in a housing assembly.
FIG. 1(b) shows an exemplary housing assembly comprising the silicon electrode sensor.

The invention relates to compositions, devices, systems, and methods for producing and using silicon electrodes modified with redox-active agents as sensors. The subject devices and systems are particularly useful for volumetrically measuring concentrations of an analyte of interest. The sensors of the present invention utilize a silicon electrode comprising redox-active species on its surface. At least one redox-active species on the silicon surface has a redox potential (reduction potential or oxidation potential) that is sensitive to the presence and or amount of an analyte of interest. Voltammetry can be performed on the silicon electrode and used to measure the redox potential of the analyte-sensitive redox groups on the surface of the electrode. The measured value of the redox potential can then be used to determine the concentration of an analyte, for example an analyte in solution. In some embodiments, the silicon electrode of the present invention has more than one redox-active species. In one aspect and at least one redox-active species is sensitive to an analyte and another redox-active species is insensitive to the presence of the analyte. Another aspect of the invention relates to the measurement of the concentration of hydrogen ion, or pH using the subject devices or systems. The surface modified silicon sensors of the present invention can be used to measure the pH of a variety of solutions. The surface modified sensors of the present invention are robust, reliable, accurate, and/or can be made such that they do not require calibration.

One advantage of using silicon as an electrode is that silicon is amenable to mass production. In particular, semiconductor processing techniques are readily available for producing silicon electrodes in large quantities at low cost. In addition, existing semiconductor processing techniques make it feasible to integrate electronic functionality into the material comprising the silicon electrode. Another advantage of silicon is that it can form strong covalent bonds, for example with carbon, nitrogen, oxygen, thus allowing for the facile and robust modification of the surface in a manner required for its intended uses. For instance, a silicon surface can be modified to attachment of any redox-active known in the art and/or described herein. Silicon is also an advantageous surface for carrying out voltammetry because it is stable to a wide range of electrical potential without degradation.

One aspect of the present invention is a surface modified silicon redox sensor for in-line monitoring applications, for example, in-line pH monitoring. The sensors of the present invention can be produced such that they do not require calibration. The ability to use the devices without calibration has a number of advantages for in-line monitoring. For example, it allows for ease of operator handling for single point measurements. In some embodiments, the sensors of the present invention are included in in-line operator-independent control measurements. Such in-line measurements can be made independent of the operator and can be used for process control, for example for pH measurements for process control. The subject sensors can be set to provide real-time measurements of an analyte, including, but not limited to real time-measurements of hydrogen ion concentration.

Silicon Substrate

One aspect of the invention is a silicon substrate having a surface onto which are attached redox-active moieties. The silicon substrate can comprise amorphous silicon or silicon comprising a variety of crystalline forms. The silicon substrate can also be polycrystalline. In some embodiments the silicon substrate can have both amorphous and crystalline regions. Where the silicon substrate is crystalline, the surface of the silicon substrate can have various crystalline faces on the surface. Crystalline silicon is generally in a face centered cubic (fcc) form. In some embodiments, such as where a polycrystalline silicon is used, the surface may have multiple crystalline planes exposed. Where single crystal silicon is used, in some cases, the silicon substrate can be made to have one or more crystal planes predominantly represented on the surface. In some embodiments, the surface of the silicon substrate will comprise one or more crystal planes having a crystalline lattice of (xxx) wherein x=0 or 1. In some embodiments the crystal planes (100), (110), (010), (001), or (101) will be predominantly represented at the surface. In some embodiments a silicon substrate has the (100) plane predominantly represented at the surface.

The silicon electrode of the present invention can comprise a polished or an unpolished silicon substrate. Silicon is generally polished prior to silicon processing, for example, building features such as transistors. In some embodiments, such as those embodiments where electronic functionality is incorporated into a silicon sensor, a polished silicon surface may be desirable. In other embodiments, an unpolished silicon substrate can be used. An unpolished silicon substrate is typically less expensive than a silicon substrate that has gone through a polishing step, and an unpolished silicon substrate can have a higher surface area for a given area of silicon than a polished silicon substrate.

The silicon electrode of the present invention can comprise a porous silicon. An advantage of porous silicon is an increase of the effective surface area. An increased surface area can be advantageous for providing a higher signal from the oxidation and reduction of the surface bound redox moieties due to a higher number of such moieties in contact with the sample. As is known in the art, if the surface is too highly porous, it can become less robust. Therefore the level of porosity can be controlled in order to maximize important properties for the particular applications. The porous silicon can be prepared by, for example, galvanostatic, chemical, or photochemical etches from silicon wafers. In some embodiments, chemical etching with hydrofluoric acid (HF) can be used to produce a porous silicon substrate. In some embodiments, the average pore size of the silicon substrate ranges from 1 nm to 500 nm. Pore size can be measured by, for example, nitrogen gas adsorption or Hg porosimetry. In some embodiments, the amount of porosity ranges between 1% and 98%. In some embodiments, the amount of porosity ranges between 5% and 75%. In some embodiments, the amount of porosity ranges between 10% and 50%. In some embodiments, the amount of porosity ranges between 20% and 40%. In some embodiments the porosity is between about 1% to about 5%, about 5% to about 10%, about 10% to about 30%, about 20% to about 40%, about 30% to about 50%, or about 40% to about 60%. The porosity measurement can be made on an area percent basis or a volume percent basis.

In addition, porous silicon could be readily integrated with existing silicon-based integrated circuit (IC) manufacturing processes.

The silicon substrate can be in any form that is amenable to the production of a silicon electrode. The silicon substrate can comprise a monolithic piece of silicon, a coating of silicon deposited onto another material, or a powder of silicon particles. The silicon substrate can be a monolithic form such as a chip, wafer, rod, needle, block, or the like. The silicon substrate can alternately be in particulate form, for example in the form of powder comprised of particles. The particles can be of arbitrary shape or can be in the form of fibers, sheets, beads, discs, or balls. Where the substrate is in the form of a powder made up of particles, it will generally be formed into a composite electrode as described in more detail below.

In some embodiments the silicon electrode is made from single crystal silicon. The single crystal silicon can be made by zone melting, also called zone refining, a process in which rods of metallurgical grade silicon are first heated to melt at one end. Then, the heater is typically slowly moved down the length of the rod, keeping a small length of the rod molten as the silicon cools and re-solidifies behind it. Since most impurities tend to remain in the molten region rather than re-solidify, when the process is complete, most of the impurities in the rod will typically have been moved into the end that was the last to be melted. This end is then cut off and discarded, and the process repeated if a still higher purity is desired. The single crystal silicon of the invention can also be produced via the Czochralski process, (CZ—Si) which tends to be inexpensive and is capable of producing large size crystals.

In some embodiments the silicon electrode is polycrystalline. As used herein, the term "polysilicon" is used interchangeably with the term "polycrystalline silicon". In some embodiments, the polysilicon is deposited. The polycrystalline silicon can be deposited by LPCVD, plasma-enhanced chemical vapor deposition (PECVD), or solid-phase crystallization (SPC) of amorphous silicon in certain processing regimes These processes require relatively high temperatures, usually above 300° C. These temperatures can make deposition of polysilicon possible substrates such as glass, but not usually for plastic substrates. The polycrystalline silicon electrodes can also be made, for example on polymeric substrates, using laser crystallization to crystallize a precursor amorphous silicon (a-Si) material on a plastic substrate without melting or damaging the plastic. In some cases, the for example, short, high-intensity ultraviolet laser pulses are used to heat the deposited a-Si material to above the melting point of silicon, without melting the entire substrate. By controlling the temperature gradients, the crystal size on the electrodes can be controlled. Grain sizes can be, for instance from about 10 nanometer to 1 micrometer. Another method to produce poly-Si at low temperatures for the electrodes of the present invention is a metal-induced crystallization in which an amorphous-Si thin film is crystallized, for example at temperatures at or above 150° C., while in contact of a metal film such as aluminum, gold, or silver. The polycrystalline silicon electrodes can also be formed onto a metal structure such as a wire. For example, the end of a cylindrical wire can be coated with polysilicon, which can be derivatized with redox active species as described herein. The structure can be used as an electrode or portion of an electrode with silicon portion accessible to the medium containing the analyte, and the wire acting to connect the silicon electrode to the parts of the system providing voltage and allowing for the flow of current.

An advantage of polysilicon over a-Si is that the mobility of the charge carriers can be orders of magnitude larger than in single crystal silicon and the material also can show greater stability under electric field and light-induced stress.

The silicon substrate of the present invention can be a thin layer of silicon that is formed upon another material, for example a thin layer of silicon formed on glass would constitute a silicon substrate.

In some embodiments the silicon substrate used to make the electrode is a composite material comprising silicon particles dispersed in a matrix or binder. The silicon substrate can be made of a composite material comprising a powder of silicon dispersed in a binder to make a composite silicon substrate. The silicon powder can be in the form of spheres, crystallites, rods, fibers, or any other arbitrary shape. In one embodiment the composite electrode is made of silicon crystallites dispersed in a polymeric matrix. The matrix or binder can be an organic, inorganic, or organometallic polymer. Non-limiting examples of useful inorganic polymeric materials include polyphosphazenes, polysilanes, polysiloxane, polygeremanes, polymeric sulfur, polymeric selenium, silicones, and mixtures of any of the foregoing.

In some embodiments the polymer can be an organic polymer. Non-limiting examples of suitable organic polymeric materials include, but are not limited to, thermoset materials and thermoplastic materials. Non-limiting examples of polymers useful in the invention include polyesters such as polyethylene terephthalate, polybutylene terephthalate, and polyethylene naphthalate, polycarbonates, polyolefins such as polyethylene, polypropylene, and polyisobutene, acrylic polymers such as copolymers of styrene and an acrylic acid monomer, and polymers containing methacrylate, polyamides, thermoplastic polyurethanes, vinyl polymers, polyimides, polyamides, polytetrafluoroethylene and other fluoropolymers, and mixtures of any of the foregoing.

The binder can be insulating, semiconductive, or conductive. In one embodiment, the binder is a material, such as a polymer, which is an insulating material. Where an insulating binder is used, the current will tend to only flow through the dispersed silicon powder. In some embodiments, the binder includes conductive components. In some embodiments, the binder comprises a conductive polymer such as polyaniline, polyacetylene, poly(allylthiophene), poly(alkylpyrrole) and the like. In some embodiments, the conductive component can comprise conductive particles such as metal particles, such as nickel particles other conductive particles including carbon particles. In some embodiments, the conductive component is chosen such that the conductive component such as the conductive polymer exhibits reduction and/or oxidation potentials that are outside of the reduction and/or oxidation potentials of the redox active moieties.

The composite silicon substrate can be formed by mixing the silicon powder with a monomer, oligomer, or prepolymer and curing the monomer, oligomer or prepolymer to form a polymeric matrix. The polymerization can be initiated in any manner known in the art or disclosed herein. The polymerization can be initiated, for example, thermally or photochemically in the presence of an initiator. The polymerization can be carried out with one or more crosslinkers. The crosslinkers can be used to tailor the physical properties of the polymeric matrix and of the composite silicon substrate. The composite silicon substrate can be formed by mixing the silicon powder with a molten thermoplastic polymer, forming the substrate, and allowing the mixture to cool. The composite silicon substrate can be formed by mixing the silicon powder with a polymer or prepolymer in a solvent, and allowing the solvent to evaporate to form the composite. Combinations of any of the above methods can be used.

The electrical properties of the composite silicon substrate can be affected by the amount of silicon, the particle size, and the particle shape. In general, the amount of silicon in the composite is high enough to create conductive pathways throughout the material. This amount of material necessary to provide conductive paths across the material is sometimes called the percolation threshold. The amount of silicon particles for conductivity can also depend on the processing conditions such as the viscosity of the binder and the amount of mixing. The amount of silicon is generally set at level at which the physical properties of the material, such as mechanical strength and flexibility will not suffer to the point that the material is not useful. The amount of silicon will generally be from about 0.1 volume percent to about 70 volume percent of the composite material. In some embodiments the amount of silicon will be from about 1 volume percent to about 50 volume percent. In some embodiments the amount of silicon will be from about 10 volume percent to about 40 volume percent. The amount of silicon can be from about 1% to about 5%, about 5% to about 10%, about 10% to about 15%, about 10% to about 20%, about 20% to about 30%, about 30% to about 40%, about 40% to about 50% or about 50% to about 60%.

The composite silicon substrate can be formed by methods used for shaping polymeric materials such as coating, molding, and casting into shapes that are useful as electrodes. The composite silicon substrate electrode will generally be connected to an electrically conductive wire in order to apply current and potential. The material can be cast, coated, and/or molded onto a conductive substrate such as a metal to form a conductive junction for connecting conductors for transfer of current to and from the composite electrode.

The silicon substrates of the invention are generally electrically conductive in order to act as electrodes, and to provide current for the oxidation and/or reduction of the bound redox-active moieties. In order to make the silicon substrate conductive, the silicon substrate will generally include impurities or dopants in order to increase electrical conductivity. Where polycrystalline silicon is used, the polycrystalline silicon electrode can either be deposited as doped polycrystalline silicon (in situ doped) or can be deposited undoped and subsequently doped with an impurity dopant such as phosphorus or boron by ion implantation or a thermal diffusion process. Dopant impurities, such as phosphorus and boron, tend to diffuse much more rapidly along the grain boundaries than they do through the silicon itself.

The dopant can be, for example, either an electron donor or an electron acceptor. Suitable electron donors are phosphorous, arsenic, antimony, and bismuth. In some embodiments the dopant is phosphorous. In some embodiments the dopant is antimony. Suitable electron acceptors are boron, aluminum, gallium, and the like. In some embodiments, the dopant is boron. In some embodiments, electron acceptors can impart a chemical resistance to the silicon electrode.

Where the silicon substrate is a monolithic material such as a wafer, the dopant can be either distributed throughout the bulk of the silicon, or can be limited to the surface region of the silicon wafer. In some embodiments, for example where the silicon substrate comprises multiple zones with different redox active moieties, the dopant can be distributed such that isolated regions of the surface of the silicon substrate are conductive.

The dopant is generally present in an amount greater than 0.01 weight percent of the silicon, and generally in an excess of about 0.1 percent of the silicon. Generally, the dopant is less than about 3 weight percent of the silicon, and almost always less than about 6 weight percent of the silicon. The presence of small amounts of the dopant can increase the electrical conductivity.

The electrical conductivity (resistivity) can be for example 0.1 (ohm-centimeters), 1 (ohm-centimeters), 10 (ohm-centimeters), 100 (ohm-centimeters), to in excess of 1000 or even 10,000 (ohm-centimeters) or even higher which is comparable to graphite and conventional metallic conductors.

In some embodiments the resistivity of the silicon substrate is the range of about 0.01 to about 1000 $\Omega$-cm. In some embodiments the resistivity of the silicon substrate is within the range of about 1 to about 100 $\Omega$-cm. In some embodiments the resistivity of the silicon substrate is within the range of about 10 to about 90-$\Omega$ cm. In some embodiments the silicon substrate is single crystal silicon is Si(100) that is p-type with a resistivity of about 10 to about 90 $\Omega$-cm. In some cases several silicon substrates with different resistivities will be used. For example, a system of the invention may comprise a one lightly doped silicon substrate having one redox active species bound to it, and also a more highly doped silicon surface having another redox active species bound to it. For example, a system of the invention may comprise one lightly doped silicon surface having a pH sensitive redox active moiety such as anthraquinone bound thereto, and a second silicon surface that is more highly doped having a hydrogen ion insensitive redox active moiety such as ferrocene bound to it.

In some cases, for example, where the silicon substrate is a cast silicon, the silicon substrate will include, for example, a silicide of a transition metal in order to provide castability. The silicide of the transition metal can provide favorable mechanical properties to the cast alloy. Typical metals useful in providing the transition metal silicide present in the silicon electrode of the secondary cell of this invention include titanium, zirconium, hafnium, vanadium, columbium, chromium, molybdenum, tungsten, manganese, iron, cobalt, nickel, copper, ruthenium, rhodium, palladium, osmium, iridium, platinum, gold, and silver. Most commonly, the transition metal present as the silicide in the silicon alloy will be a silicide of manganese, chromium, iron, cobalt, nickel, or molybdenum. The amount of the silicide will be sufficient to provide satisfactory castability but not great enough to deleteriously effect the properties of the silicon, i.e., from about 2 percent or more up to as high as 30 percent transition metal, elemental basis.

Redox-Active Moiety

In one embodiment, the subject silicon surface comprises a surface modified with redox-active functional groups. At least one redox-active functional group on the surface is sensitive to the presence and or the level of a substance in the solution. In some embodiments, the silicon surface will have at least one redox-active functional group sensitive to an analyte, and at least one redox-active functional group that is substantially insensitive to the analyte to be tested. When used in this manner, the substantially insensitive group can act as a reference, allowing for greater accuracy and reproducibility of the measurements.

The redox groups can be chemically or physically bound to the surface. The redox groups can be attached to the silicon covalently, can be adsorbed to the silicon, or can be attached to polymers that are either covalently or non-covalently bound to the surface. Covalent binding of either the redox group or the polymer to which the redox group is a part can be beneficial in improving the lifetime and stability of the electrode. Silicon can form covalent bonds with carbon, and thus is a desirable substrate for functionalizing with carbon based molecules. The covalent binding to the surface can be through a bond between silicon and carbon, oxygen, nitrogen, sulfur, or other atom. In some embodiments the bond is between silicon and carbon. In some embodiments the bond is between silicon and oxygen. The physical bonding can occur through adsorption, and can include, for example, spontaneous self assembly onto the silicon surface of molecules such as those derived from fatty acids which comprise redox active moieties.

Where a linker group is used, the linker can be small, for example one to 3 atoms, or can be longer, e.g. 20 to 100 atoms, or can be any size between large and a small linker. Where a short linker is used, the redox-active moiety is held close to the surface. Where a longer group is used, the redox active moiety may be able to move away from the surface, for example into the solution. Linker groups can comprise hydrophilic, hydrophobic groups, or mixtures thereof. Linker groups can comprise, for example, hydrocarbons, esters, ethers, amides, amines, carbonyls, thiols, olefins, silicones, or other organic, inorganic or organometallic groups. The linker groups can be formed by polymerization or oligomerization reactions such as free radical or anionic polymerization. The linker group can comprise, for example, ethylene oxide, propylene oxide, or acrylamide repeat units. Linkers can have ring structures including aromatic rings. The variation in the linker structure can be used to vary the mobility of the redox-active moiety in the solution.

As used herein, the term moiety generally refers to a portion of a molecule or substituent. A redox-active moiety may be highly substituted, and can still act as a redox-active moiety. As used herein, the terms "redox active moiety", "redox active group", "redox active functional group", and "redox group" are used interchangeably. Thus, for example, the redox-active moiety ferrocene includes substituted ferrocenes, ferrocene polymers, and ferrocene covalently attached to the surface with or without linker molecules.

In some embodiments, the redox-active moiety can be incorporated into a polymer, and the polymer comprising the redox active moiety can be immobilized onto the silicon surface. The immobilization of the polymer can be either chemical or physical. The immobilization of the polymer can be through covalent bonds, or through adsorption of the polymer to the silicon surface.

In some embodiments, the redox-active moiety is bound to a particle that is bound to silicon. The particle is generally an electrically conductive particle. The particle attached to the silicon surface in a manner that allow for current to flow between the silicon surface and the particle. The particles can be attached chemically or physically to the surface. For example, the redox-active moiety can be attached to a carbon particle, and the carbon particle attached to the silicon surface. In some embodiments, the carbon particle can be a carbon nanotube. In some embodiments of the invention, carbon nanotubes can be attached to the surface of the silicon, where there are redox-active groups attached to the carbon nanotubes. For instance, attachment of well-aligned single-walled carbon nanotubes architecture to a single-crystal silicon surface can be used. In some embodiments, for example, ferrocenemethanol molecules are attached to single walled carbon nanotube (SWCNT) arrays that are directly anchored to the silicon surface, for example, a (1 0 0) surface. For example, single wall carbon nanotubes can be coupled to the surface using this method as described in Yu et al., Electrochimica Acta 52 (2007) 6206-6211.

The redox-active moieties generally have reversible redox activity with well-defined cyclic voltammetry oxidation and/or reduction peaks. A suitable reference redox reagent can vary from application to application or medium to medium depending on the intended use.

The position of the reduction and/or oxidation potentials of the redox active moiety can be chosen in order to improve the accuracy and quality of the measurement of redox potential. In some cases, the reduction and or oxidation potential can be chosen to be away from other redox active species. The silicon surface generally has a wide window in which to perform measurement of reduction or oxidation potential without interfering with the measurement of the reduction and or oxidation of the redox active moieties bound to the surface. The silicon surface can generally be used to measure oxidation and/or reduction potentials from between about negative 2 V to about positive 2 V. In some cases, for example where the medium is an aqueous medium, the reduction and/or oxidation potential of the redox-active moiety can be chosen so as not to fall within the reduction or oxidation potential of the medium in order to minimize interference. This can be useful where cyclic voltammetry is used, and is less important when square wave voltammetry is used.

Figure 5:
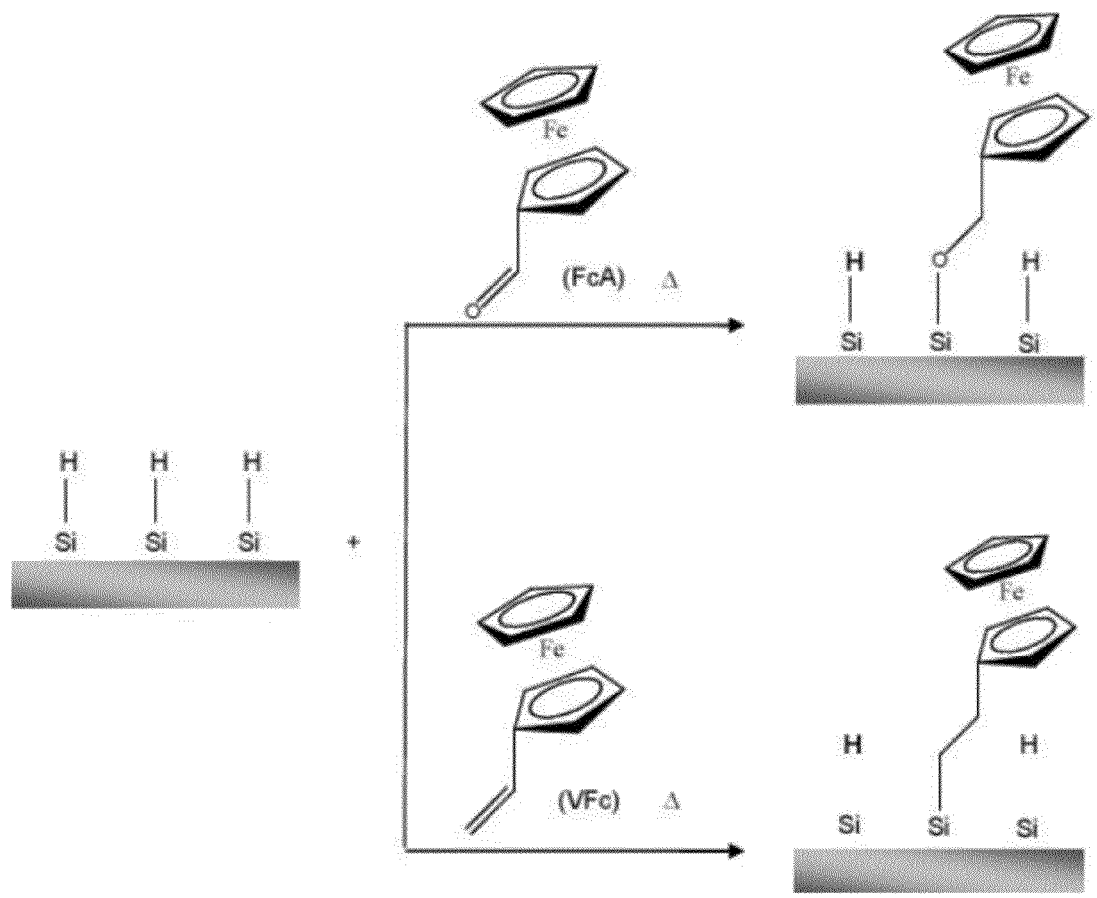
FIG. 5 illustrates a silicon surface derivatization with ferrocene moieties, VFc and FcA by thermal immobilization.

Redox-active moieties that are insensitive to the presence of analytes should show little or no change in their oxidation and/or reduction potentials in the presence or absence of such analytes. Redox-active moieties that are generally insensitive to the presence of analytes, and in particular are insensitive to the presence of hydrogen ion include: ferrocene, polyvinylferrocene, $Os(bpy)_2Cl_2$, $Ru(bpy)_2Cl_2$, viologen, polyviologen, and polythiophene. Redox reagents having molecular redox properties are generally preferable because they tend to exhibit the highest degree of Nernstian electrochemical reversibility. FIG. 5 shows examples of the hydrogen ion insensitive redox-active moiety ferrocene bound to a silicon surface.

Figure 6:
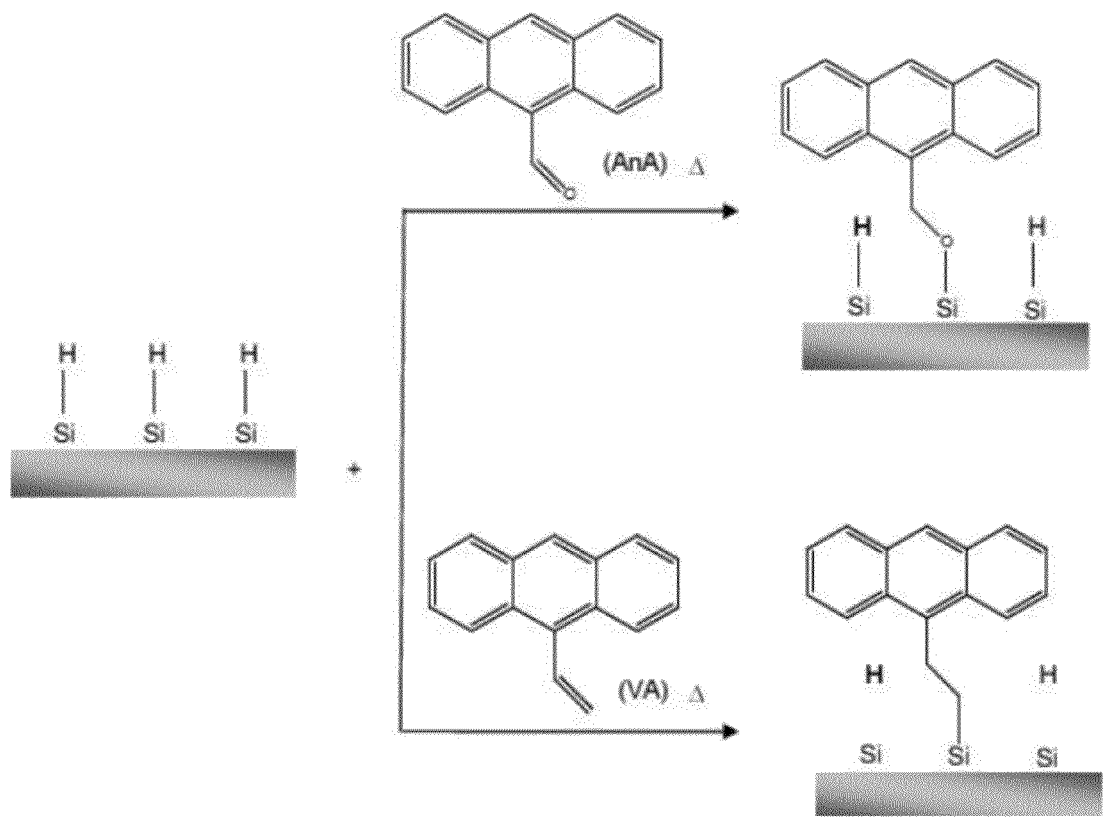
FIG. 6 illustrates a silicon surface derivatized with anthracene moieties, VA and AnA by thermal immobilization.
Figure 7:
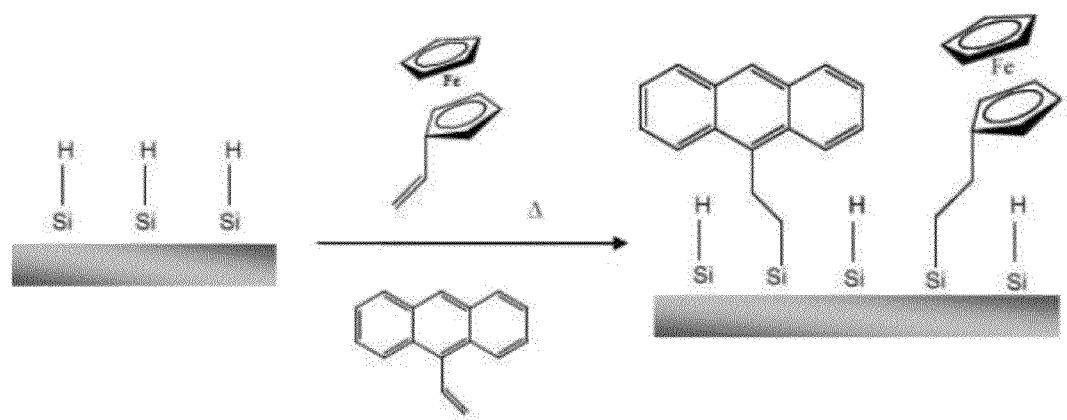
FIG. 7 illustrates a silicon surface derivatized with both the anthracene (VA) and ferrocene (VFc) moieties by thermal immobilization.

Non-limiting redox-active moieties that are sensitive to hydrogen ion include: quinones, anthroquinones. phenanthroquinones, phenylene diamines, catechols, phenothiazinium dyes, and monoquaternized N-alkyl-4,4'-bipyridinium. In some embodiments the redox-active moiety that is sensitive to the presence of hydrogen ion can include inorganic materials and metal oxides. Hydrogen ion sensitive inorganic redox-active inorganic moieties include Prussian Blue, $Ni(OH)_2$, and $RuO_x$. FIG. 6 shows examples of the hydrogen ion sensitive redox-active moiety anthracene covalently bound to a silicon surface. FIG. 7 shows an example of a silicon surface having covalently bound thereto both the hydrogen ion sensitive redox-active moiety ferrocene and the hydrogen ion insensitive redox-active agent anthracene.

In some embodiments the analyte is carbon monoxide (CO). An example of a CO sensitive redox-active agent is ferrocenyl ferraazetine disulfide. A CO insensitive redox-active agent can be, for example, ferrocene.

In some embodiments the analyte is an alkali metal. Alkali metal sensitive redox-active agents include, for example: 1,1'-(1,4,10,13-tetraoxa-7,16-diazacyclooctadecane-7,16-diyldimethyl), ferrocenyl thiol, and other ferrocene derivatives containing covalently attached cryptands. These materials are described, for example, Hammond, et al., J. Chem. Soc. Perkin. Trans. I 707 (1983); Medina, et al., J. Chem. Soc. Chem. Commun. 290 (1991); Shu and Wrighton, J. Phys. Chem. 92, 5221 (1988). Included are examples such as the above ferrocenyl ferraazetine and ferrocenyl cryptand, in which an ordinarily chemically insensitive redox center (ferrocene) is covalently linked to a chemical recognition site in such a way as to make it's redox potential chemically sensitive. Also suitable are molecules or polymers in which the sensor and reference functionalities are covalently linked such as 1-hydro-1'-(6-(pyrrol-1-yl)hexyl)-4,4'-bipyridinium bis(hexafluorophosphate), as described by Shu and Wrighton, J. Phys. Chem. 92, 5221 (1988).

In some cases, more than one analyte-sensitive redox-active moiety can be used. For example, there can be one redox-active moiety that is sensitive to hydrogen ion, and another that is sensitive to a second analyte such as CO, oxygen, ammonia, or an alkali metal. This approach allows for the simultaneous measurement of several analytes. In some cases redox-active agents sensitive to 3 or more analytes can be used. Where there are redox agents sensitive to multiple analytes, in many cases, it is also desired to have one or more analyte-insensitive redox-active moieties bound to the silicon surface as well to provide a reference, to improve accuracy, and to minimize or avoid calibration.

Where more than one redox-active moiety is used it can be important to ensure that the oxidation and reduction potentials are far enough apart such that there is not significant interference between the peaks. This can be desirable especially when the multiple redox-active moieties are on the same electrically addressable zone on the silicon substrate.

In some embodiments, the silicon substrate has a plurality of isolated separately electrically addressable zones. In some embodiments, the different zones will comprise different redox-active moieties. The use of separate zones can be beneficial in that the voltammetric measurements can be carried out separately, allowing for the use of multiple redox-active agents with that have similar reduction and/or oxidation potentials.

The separately electrically addressable zones can be made by conventional semiconductor processing methods, for example masking to create structures in specific areas on the surface, for example specific areas on the surface having certain levels of doping. Conventional semiconductor processing can also be used to incorporate conductive traces allowing the zones to be separately addressable. Masking can also be used during the attachment of the redox-active moieties to the silicon surface to attach specific redox active moieties to different regions of the surface.

The silicon substrate with separately addressable zones can effectively create an electrochemical sensor array. One aspect of the invention is a silicon electrochemical sensor array wherein a plurality of zones, each zone comprising a redox active moiety. The array can have multiple zones with analyte-sensitive redox-active moieties, and one or more zones with analyte-insensitive redox active moieties. A zone can have a single redox-active moiety, or multiple redox active moieties. The array can be constructed, for example, to measure both pH and $O_2$, wherein one zone comprises a redox-active moiety sensitive to hydrogen ion, another zone has a redox active moiety sensitive to $O_2$, and a third zone with a redox-active moiety that is insensitive to both hydrogen ion and $O_2$.

The silicon substrate of the invention can also comprise circuitry. The circuitry can be used, for example for controlling the current and potential provide to the redox-active moiety. The circuitry can also be used for analyzing signals or for processing data related to the voltammetric measurement. The circuitry can also have other functionality, such as the ability to measure other parameters such as temperature, the ability to store date, or the ability to send data and receive instructions from a remote location.

Silicon Electrode Sensor

An aspect of the invention is the incorporation of the silicon substrate described above into a silicon electrode sensor. The silicon electrode sensor comprising the silicon substrate can be used for the measurement of the presence or absence of one or more analytes, or can be used to accurately measure the concentration of analyte in a sample.

The silicon electrode sensor of the invention can be used to measure analytes including hydrogen ion, alkali metals, CO, or $O_2$. In some embodiments, the silicon electrode sensor is used to measure the concentration of hydrogen ion, or pH.

The silicon electrode sensor comprises a silicon substrate as described above comprising a redox-active moiety that is sensitive to the presence of an analyte. The silicon electrode sensor may also comprise a redox active moiety that is insensitive to the presence of an analyte. The silicon electrode sensor can comprise more than one silicon substrate. For example, the sensor may comprise one silicon substrate that has an analyte sensitive redox active moiety and another silicon substrate having an analyte insensitive redox active moiety.

The silicon electrode sensor is configured to be incorporated into a system that will supply voltage, and can drive current to the sensor in order to perform voltammetry. Thus, the silicon substrate or substrates within the sensor will be electrically connected in a manner which will allow for connection to a device for supplying and measuring current and voltage.

The silicon electrode sensor is generally the working electrode in an electrochemical system that will also comprise a counter electrode, and in some embodiments, a reference electrode.

The sensor will be put into contact with a sample having the analyte to be detected. The sample is generally a liquid sample. In some cases the sample can be a gel, suspension, molten, or semi-solid medium. The sample can be any type of liquid including hydrocarbons, oils, fluorocarbons, silicones, and aqueous solutions. Where the analyte is hydrogen ion, an aqueous medium is generally used, but in some case a polar protic medium or polar aprotic medium can be used. The sensor is useful for measuring pH in aqueous solutions.

In some embodiments, the sensor of the invention can accurately measure analyte concentrations where the analyte is present in a concentration range from about $10^{-2}$ M to about $10^{-13}$ M. In some embodiments, the sensor of the invention can accurately measure analyte concentrations where the analyte is present in a concentration range from about $10^{-3}$ M to about $10^{-10}$ M. In some embodiments, the sensor of the invention can measure the concentration to an accuracy of about plus or minus 100%, 50%, 30%, 20%, 10%, 5%, 2% or 1%. In some embodiments, the sensor of the invention can measure the concentration within a range of $10^{-3}$ M to about $10^{-10}$ M to an accuracy of about plus or minus 100%, 50%, 30%, 20%, 10%, 5%, 2% or 1%.

In some embodiments, the analyte is hydrogen ion, and the sensor of the invention can accurately measure the pH in a range from about pH2 to about pH13. In some embodiments, the analyte is hydrogen ion, and the sensor of the invention can accurately measure the pH in a range from about pH3 to about pH10. In some embodiments, the sensor of the invention can accurately measure pH to an accuracy of plus or minus 0.5, 0.3, 0.2, 0.1, 0.07, 0.05, 0.03, 0.02, or 0.01 pH units. In some embodiments, the sensor of the invention can accurately measure pH in a range from about pH3 to about pH10 to an accuracy of plus or minus 0.5, 0.3, 0.2, 0.1, 0.07, 0.05, 0.03, 0.02, or 0.01 pH units.

The silicon electrode sensors of the invention can accurately measure analyte concentration in a wide variety of sample types. The sensors can be made to be robust, and resistant to fouling, and therefore reliable for long-term measurements.

One aspect of the invention is a sensor which does not require routine calibration, or in some cases, any calibration at all. Conventional potentiometric sensors rely on a glass membrane to sense, for example, hydrogen ion. These types of sensors generally need to be calibrated on a regular basis, usually by placing the sensor into standards of known pH. These types of sensors generally need calibration when going from one solution to another solution, and will also need calibration with time, even if kept within the same solution and even upon standing outside of a solution. The situation is made worse if there is a change in the composition of the medium over the time that the sensor is monitoring the medium, for example, when monitoring a chemical reaction, biochemical reaction, or fermentation. In these cases, potentiometric sensors may drift and need calibration due to the accumulation of some species in the reaction, or due to precipitation of species onto the sensor.

In some embodiments, the sensors of the present invention do not need to be calibrated under any of these situations. In some embodiments, the sensors of the invention do not need to be calibrated over time in solution. In some embodiments, the sensors of the invention do not need to be calibrated after an hour, 10 hours, 1 day, 2 days, 5 days, a week, two weeks, a month, 6 months, 1 year, 2 years or longer while in a solution or in storage. In some embodiments the sensors or the present invention are accurate at measuring analyte concentration to 50%, 40%, 20%, 10%, 5%, 2%, 1%, 0.5%, 0.2% or 0.1% after the times above. In some embodiments where the sensors measure pH, the sensors are accurate to 1, 0.8, 0.5, 0.3, 0.2, 0.1, 0.08, 0.05, 0.03, 0.02, or 0.01 pH units after the times above. In some embodiments where the sensors measure pH, the sensors are accurate to within 0.1 pH units after one week in solution or in storage.

In some embodiments, the sensor is capable of measuring analyte concentration without any calibration with an external standard. In some embodiments, the sensor remains sensitive to the analyte without calibration after a first use by an end user.

In some embodiments the analyte is hydrogen ion and the sensor remains sensitive to hydrogen ion after exposure to a cell culture medium for at least about 1, 3, 6, 9, 12, 18, or 24 hours or 2, 3, 4, 6, 8, 12, 24, 48, 60, 90, or more days. In some embodiments the analyte is hydrogen ion and the sensor remains sensitive to hydrogen ion after exposure to a cell culture medium for at least about 3 days. In some embodiments the analyte is hydrogen ion and the sensor remains sensitive to hydrogen ion after exposure to a cell culture medium for at least about 6 days. In some embodiments, the sensor is capable of measuring pH with an accuracy of 0.2 units after exposure to the cell culture medium.

In some embodiments, the analyte is hydrogen ion and the sensor is capable of measuring pH with an accuracy of 0.2 units after autoclave treatment at 121° C. for 10, 20, 40, 80, 100, 200, 400, or 800 minutes. In some embodiments, the analyte is hydrogen ion and the sensor is capable of measuring pH with an accuracy of 0.2 units after autoclave treatment at 121° C. for 40 minutes. In some embodiments, the analyte is hydrogen ion and the sensor is capable of measuring pH with an accuracy of 0.2 units after autoclave treatment at 121° C. for 400 minutes.

A subject sensor that does not require calibration over long periods of time in a medium that can change characteristics is useful, for example, as an implantable sensor. The implantable sensor can be placed under the skin or within the body in contact with a bodily fluid such as blood, saliva, breast milk, amniotic fluid, lymph, sweat, tears, or urine. The sensor can measure the concentration of analytes such as hydrogen ion, sodium, potassium, or oxygen.

The implantable sensor has an electrode configured to be in contact with a bodily fluid, said electrode comprising a silicon surface that has immobilized thereon a redox active moiety, wherein the redox active moiety has an oxidation potential and/or reduction potential that is sensitive to concentration of said ion. The implantable sensor can be included in an implantable medical device such as described in U.S. Pat. No. 6,738,670. For example, the implantable medical device in which the sensor resides could include pacemakers, defibrillators, drug delivery pumps, diagnostic recorders, cochlear implants, and the like. The implantable medical device is typically programmed with a therapy and then implanted in the body typically in a subcutaneous pocket at a site selected after considering clinician and patient preferences. In some embodiments the implanted device is in a form which can be swallowed, allowing the measurement of the properties of the regions encountered as it passes through the body such as of the stomach, the digestive tract including the upper and lower intestines, and the colon. The information obtained by the sensor in the implanted device can either be accessed in real time, for example, by wireless communication, or can be retrieved from the device after passage through the body. A wide variety of programmers, also known as downlink transmitters, can be used to transmit data to and receive data from the implantable medical device. Examples of downlink transmitters include devices such as physician programmers, patient programmers, programming wands, telemetry access units, and the like. The clinician, for example, can periodically use a physician programmer to communicate with the implantable medical device to manage the patient's therapy and collect implantable medical device data. The silicon electrode sensor can be incorporated into or attached to the implantable medical device and can provide data on analyte concentration within the region of the body into which it is implanted. The patient can use the patient programmer to communicate with the implanted device to make therapy adjustments that have been programmed by the clinician. Both the physician programmer and patient programmer can have an antenna locator that indicates when a telemetry head is aligned closely enough with the implanted device for adequate telemetry.

An aspect of the invention is a method of measuring concentration in a bodily fluid within a body comprising placing a silicon electrode sensor comprising a redox active moiety in contact with the bodily fluid; and operating the sensor to yield a value of the concentration of the analyte present in said bodily fluid.

System

One aspect of the invention is a system for measuring analyte concentration. In one embodiment, the system comprises: a working electrode having a silicon surface that has immobilized thereon a redox active moiety, wherein the redox active moiety has an oxidation potential and/or reduction potential that is sensitive to the presence of an analyte; a counter electrode and optionally a reference electrode; a source for supplying a plurality of potentials to the working electrode; and a device for measuring current through the working electrode at the plurality of potentials. The working electrode referred to herein can comprise the silicon electrochemical sensor described above. It is desirable in many embodiments that the silicon surface also has immobilized thereon a second redox active moiety having an oxidation potential and/or reduction potential that is insensitive to the presence of said analyte. The redox active moiety that is insensitive to the presence of the analyte can be on the same silicon surface, or can be on another surface in electrical contact with the system and in contact with the sample. The system is configured such that the working electrode, the counter electrode, and optionally the reference electrode are in contact with the sample. In many embodiments, the sample is a liquid sample, and the electrodes are each in contact with the liquid. In some cases, the sample will not be a liquid, but will be a solid, generally comprising a solid electrolyte, or a gas.

In some embodiments, the system will have two or more working electrodes. For example, in some embodiments, the system will have one working electrode comprising a silicon surface that has immobilized thereon a redox active moiety whose oxidation potential and/or reduction potential is sensitive to the presence of said analyte, and a second working electrode comprising redox active moiety whose oxidation potential and/or reduction potential is insensitive to the presence of said analyte. An example of a system with two working electrodes is a system having two silicon wafers, one of which has a redox active moiety which is sensitive to pH, such as anthracene, and another redox active moiety which is insensitive to pH, such as a ferrocene. In some cases the silicon wafer on which each redox active species is immobilized will be a different type of silicon wafer. For instance, the silicon wafer to which the pH sensitive moiety is bound may have one doping level, and the silicon wafer on which the pH insensitive moiety is bound may have a different doping level. This type of construction can be beneficial because, in some cases, one type of redox active species will perform better in terms of amplitude, sensitivity or stability with one type of doping, while another redox active species will perform better on a silicon wafer with a different type of doping. In some embodiments, the pH sensitive moiety, e.g. anthracene, is bound to a silicon wafer that has a low level of doping, and the pH insensitive moiety, e.g. ferrocene is bound to a silicon wafer that has a higher level of doping. In some embodiments the silicon wafer onto which the pH sensitive moiety, e.g. anthracene is bound has a resistivity between about 1 $\Omega$-cm to about 1000 $\Omega$-cm, or between about 10 $\Omega$-cm to about 90 $\Omega$-cm, or between about 10 $\Omega$-cm to about 40 $\Omega$-cm while silicon wafer onto which the pH insensitive moiety, e.g. ferrocene, is bound has a resistivity between about 0.001 $\Omega$-cm and 0.1 $\Omega$-cm, or from about 0.001-0.005$\Omega$ cm resistivity, about 0.02-0.05 $\Omega$-cm. In some embodiments, an N-type silicon wafer is used for the pH insensitive moiety, e.g. ferrocene. In some embodiments, an N-type silicon wafer is used for both the pH sensitive and the pH insensitive moiety.

In some embodiments, the system will have 3 or more working electrodes. For example, in some embodiments, the system will have one working electrode comprising a silicon surface that has immobilized thereon a redox active moiety that is sensitive to the presence of a first analyte, a second working electrode comprising a silicon surface that has immobilized thereon a redox active moiety that is sensitive to the presence of a second analyte, and a third working electrode comprising a silicon surface that has immobilized thereon a redox active moiety that is insensitive to the presence of either the first analyte nor the second analyte. The system can also have more than 3 working electrodes, for example having 4, 5, 6, 7, 8, 9, 10, 12, 20, 50 or more working electrodes, each having redox active moieties sensitive to and analyte. These systems can also have one or more than one silicon working electrode having a redox species that is insensitive to the analytes, for example to provide a reference. In some cases more than one redox species that it insensitive to the analyte can be used.

In some embodiments it is useful to use lightly doped silicon wafers for a moiety such as anthracene. While not being bound by theory, the band gap of the silicon can be influenced by the level of doping of the silicon, and it is believed that in some cases, the use of silicon with the appropriate level of doping can be useful in order to tailor match the appropriate redox active moiety with the appropriate band gap. Thus in some cases it is desirable to use lightly doped silicon with a moiety such as anthracene. Thus in some embodiments it is useful to use two silicon working electrodes: one optimized for Fc moieties and the other optimized for the anthracene moieties. When two working electrodes are used, in some embodiments, two sequential electrochemical measurements (e.g. with square wave voltammetry) will be carried out using the same counter and reference electrode. For instance, the first measurement can be conducted using reference, counter and working electrode 1 (anthracene derivatized) between −1.2 to −0.5 V, followed by the second measurement which will be conducted using reference, counter and working electrode 2 (ferrocene derivatized) between 0 to 0.5V. The peaks potential detected in the first and second measurements can then be stored and processed to get a pH reading. This type of system and method can be accomplished through the use of a bipotentiostat or a two-channel multiplexer. A similar approach can be applied to multiple working electrodes with a mutipotentiostat or a multi-channel multiplexer.

The system is configured to carry out voltammetric (also called amperometric) measurements on the sample. In one aspect the present invention provides a method which includes the measurement of pH with a voltammetric pH sensing system comprising the silicon electrode sensor described above, a potentiostat for providing voltage to the electrodes, and a meter for detecting the current as a function of voltage.

The counter electrode typically is needed to complete the electrochemical circuit in order to make the measurements described herein. The counter electrode is generally made of a material which is chemically inert to the medium so that its potential does not change significantly during the course of measurement. Suitable materials in many applications include platinum, gold, stainless steel, and carbon.

A reference electrode is optional and is used as a third electrode in some embodiments of the invention. In the case of a three-electrode system, the counter electrode generally completes the circuit, allowing current to flow through the cell, while the reference electrode maintains a constant interfacial potential difference regardless of the current. In the case where the system comprises an analyte sensitive redox active moiety and an analyte insensitive redox active moiety, the analyte insensitive redox active moiety can act as a reference, allowing the potential difference to be used to determine analyte concentration. Even where an analyte insensitive moiety, in some embodiments, a reference electrode will still be used. In some embodiments, pseudo-reference electrodes can also be utilized. Reference electrodes which can be employed include: Standard hydrogen electrode (SHE), also known as "normal hydrogen electrode" (NHE), saturated calomel electrode (SCE), copper-copper(II) sulfate electrode, and silver/silver chloride (Ag/AgCl) electrode. In some embodiments a silver electrode can act as a silver/silver chloride electrode where sufficient chloride is present at or near the silver electrode. In some cases, especially where a nonaqueous medium is used, a metal electrode such as a platinum or a silver electrode can be used as the reference electrode.

In order to carry out voltammetry, the system generally has a source for supplying a plurality of potentials. The voltammetry can be, for example cyclic voltammetry, pulse voltammetry, normal pulse voltammetry, square wave voltammetry, differential pulse voltammetry linear voltammetry, or square wave voltammetry. The source for supplying a plurality of potentials can be a potentiostat, for example, a potentiostat capable of applying square waves for square wave voltammetry.

Generally, the analyte concentration is determined by using voltammetry to identify the position of current peaks, which current peaks indicate the reduction or oxidation potential of a redox active moiety. In some embodiments, the position of the reduction and/or oxidation potential of the analyte sensitive redox active moiety is used to determine the concentration of the analyte. This method can be used, for example, where no analyte insensitive redox active moiety is employed.

Where an analyte insensitive redox active moiety is used, detection is generally accomplished by measuring the potential difference, delta E, associated with current peaks for oxidation (or reduction) of the immobilized redox active moieties, where the magnitude of delta E can be related to the concentration of analyte, e.g. hydrogen ion (H+) in solution. The analyte insensitive redox active moiety has an electrochemical response that is insensitive to variations in the medium and serves as the reference. Current peaks for oxidation or reduction of the reference and indicator are determined from a voltammogram using a counter electrode.

In some embodiments, the system further comprises a computation system that communicates with the device for measuring current. The computation system can have algorithms for calculating reduction or oxidation potential from the measured current at a plurality of potentials from the voltammetry measurements. The computing systems can be part of the sensing system, in some cases allowing the sensing system to be self-contained. The computing system can comprise memory for storing raw and/or processed data from the sensors. The computing system can be connected to a transmission device that will wirelessly or by wire transmit processed data to an external device. The computing system can provide signals and measurements which can be transmitted in some cases in real time, allowing the system to alert end users of conditions which may require attention. The transmitted signals and measurements can, for example, provide the information required for adjusting a manufacturing process such as a chemical or biochemical process.

In some embodiments the system is made up of a housing that holds the silicon electrode sensor which is electrically connected to a unit comprising the source for supplying a plurality of potentials and the current measuring device. In some embodiments the unit also comprises the computing system described above for at least partially analyzing the data. The unit can be battery powered, or can have a connection to an outside power source. The unit can have a display and input buttons to allow the user to control the measurement and to read the output from the sensor. The unit can have transmission capability for sending out data, and for receiving instructions or to be tested by an external device.

FIG. 1 shows drawings of an embodiment of the connection of the silicon sensor electrode into a sensor housing for use in measuring analytes in a fluid such as the fluid in a biochemical reactor. FIG. 1(a) shows a blow up drawing of an assembly that holds the silicon electrode sensor and provides electrical connections to the silicon electrode sensor for voltammetry measurements. In FIG. 1(a) the silicon electrode sensor (I), is held in place by the end cap (II), in contact with the metallized ceramic disk (III). The ceramic disk can be metallized in specific areas on both the front and the back of the disk, with vias connecting the specific metallized areas. On one side of the ceramic disk, the silicon working electrodes as well as the counter and optionally reference electrodes can be present. For example, electrodes such as the silicon working electrodes can each being mounted to a specific metallized area. The disk is then mounted into the housing such that the side of the disk having the electrodes is exposed to the medium into which the probe is immersed, and the other side of the disk is away from the medium, allowing for electrical connection to the metallized areas on to the disk such that voltage can be applied and current can flow to and from the electrodes. The sealing gasket (IV) provides sealing from the fluid in which the sensor is immersed while allowing electrical contact with the pin contacts (V) on the shaft of the housing (VI). FIG. 1(b) shows the housing assembled for insertion into the fluid to be measured. Pipe fittings are used to seal the wires that provide electrical connection to the silicon electrode for voltammetric measurements.

Figure 2:
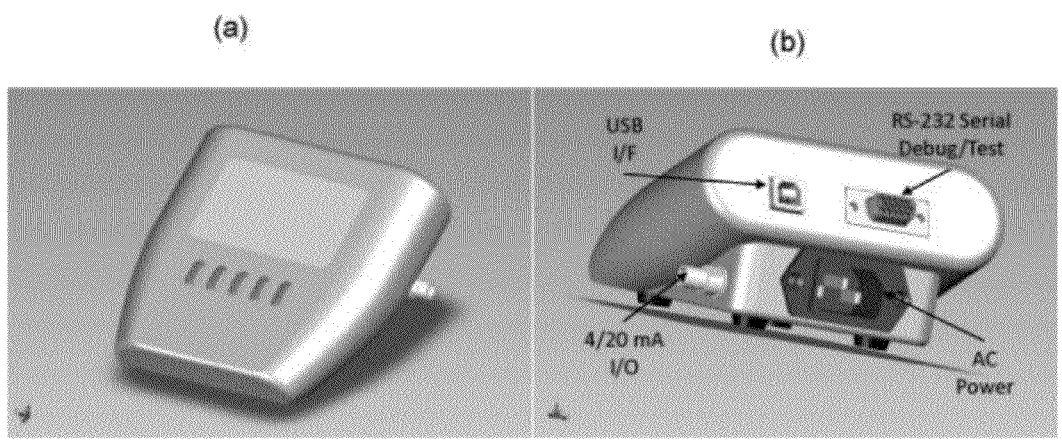
FIG. 2 depicts an embodiment of the invention comprising a unit that electrically connects to the silicon electrode sensor and comprising a source for supplying a plurality of potentials and a current measuring device.

FIG. 2 shows a drawing of an embodiment of the unit comprising the source for supplying a plurality of potentials and the current measuring device. FIG. 2(a) shows a top view and FIG. 2(b) shows a back side view. The unit has an electrical input/output connector for connecting to the electrodes for carrying out voltammetry (4/20 mA I/O). The unit has a connection for AC power. The unit has a universal serial bus interface (USB I/F) and an RS-232 Serial port for transmitting data, for receiving instructions, and for testing and debugging by an external device. The unit also comprises a liquid crystal display (LCD) and has user interface buttons to allow the user to control the measurements and to read the output from the sensor.

Figure 3:
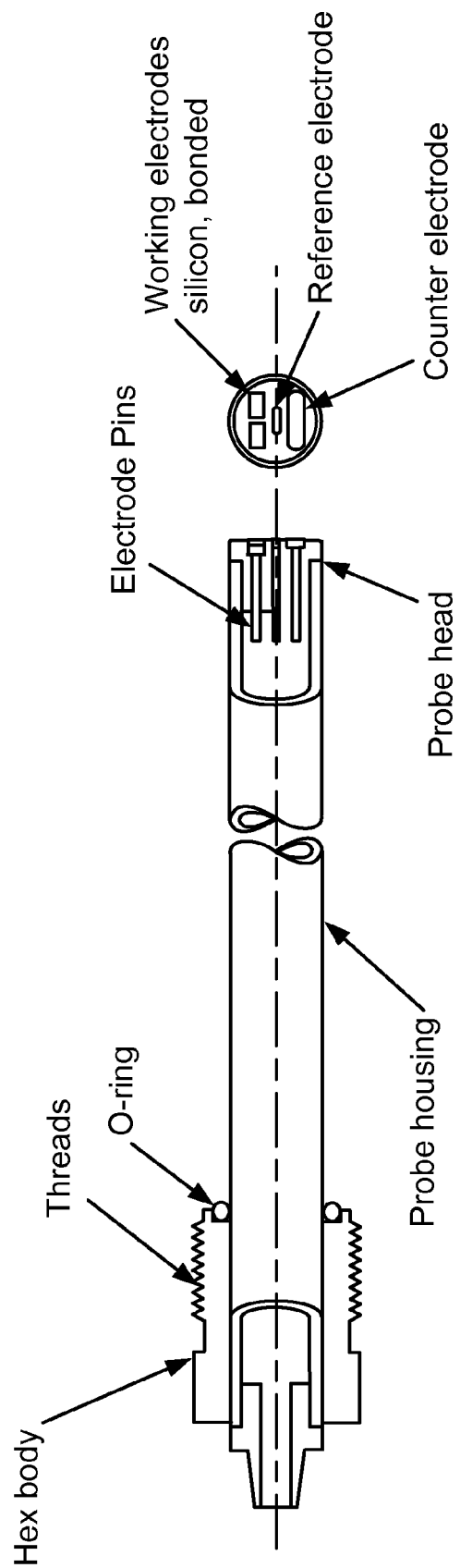
FIG. 3 depicts an embodiment of the invention comprising a probe for measuring analytes within a reactor comprising two working silicon electrodes.

FIG. 3 shows another exemplary embodiment of an aspect of the system of the present invention. FIG. 3 shows a probe that contains two working electrodes, a reference electrode, and a counter electrode. The electrodes can be electrically connected through the probe to the source for supplying a plurality of potentials to the working electrode, the counter electrode, and optionally the reference electrode, and a device for measuring current through the working electrode at the plurality of potentials. In this embodiment, the two working electrodes, the reference electrodes and the counter electrode are contained on the end of the probe on a disk which allows the electrodes to be in contact with the medium comprising the analyte(s) to be measured. The areas of the various electrodes can be varied in order to improve the performance of the system. While this embodiment shows two working electrodes, in some embodiments, there will be one working electrode, and in other embodiments, there are 3, 4, 5, 10, 20, or more working electrodes. In some embodiments one working electrode can comprise a silicon surface with a redox active moiety that is sensitive to pH, such as anthracene, and the other working electrode can comprise a redox active moiety that is insensitive to pH, such as ferrocene. In some embodiments, the silicon surface on which the pH sensitive moiety, such as anthracene, is bound comprises a silicon wafer that is lightly doped, and the silicon surface on which the pH insensitive moiety, such as ferrocene, is bound comprises a silicon wafer that is more heavily doped.

The silicon working electrodes can be bonded to conductive regions on the disk. Conductive vias through the disk allow electrical connection to electrode pins which are contained within the housing. The electrode pins are in turn, electrically connected, for example to wires, which can run through the probe housing, and then out of the housing in order to electrically connect the electrodes to the source for applying potentials to the electrode, and to the device for measuring the current that passes through the electrodes. The threads, o-ring, and hex body allow for the probe to be mounted into a reactor such as a bioreactor or fermentor. The threads allow for the probe to mate with a corresponding threaded hole through the wall of the reactor, the hex body allows for tightening the probe into the reactor, and the gasket assists in establishing a seal.

In some embodiments, the system is configured to be used as an in-line sensor in a process. An in-line sensor can be a sensor that is used in an on-going process. In some embodiments the sensor is in a vessel, in other embodiments the sensor is in a conduit or pipe through which a process fluid flows. In some embodiments, the currents measured at a plurality of potentials by voltammetry are used to determine analyte concentration, and the determined analyte concentration is used to control a process parameter. The systems of the present invention are valuable in in-line sensing in that they can be made to be robust, to resist fouling, and are able to measure analyte concentration for long periods of time in media that changes its properties, as in a process such as a chemical reaction.

Method of Making a Silicon Electrochemical Sensor

An aspect of the invention is a method of making an electrochemical sensor. The method generally comprises having a silicon substrate with a silicon surface and immobilizing a redox active moiety with a reduction and/or oxidation potential that is sensitive to an analyte onto the silicon surface.

An aspect of the invention is a method for forming an analyte-sensitive silicon electrode, said electrode having a silicon surface, the method comprising: immobilizing a redox-active moiety that is sensitive to the presence of an analyte onto the silicon surface.

Any method known in the art or disclosed herein can be used to construct a silicon surface as described above that is useful as part of a subject sensor. The redox groups can be immobilized onto the surface chemically or physically. The redox groups can be reacted with the silicon surface to attach them to the silicon covalently. Alternatively, the redox active groups can be adsorbed to the silicon. The redox active groups can also be immobilized by attaching the groups to a polymer that is either covalently or non-covalently bound to the surface. Covalent binding of either the redox group or the polymer to which the redox group is a part to the surface can be beneficial in improving the lifetime and stability of the electrode.

Methods are known for covalent attachment of functional groups to silicon. Silicon can, for example, form covalent bonds with carbon, and thus is a desirable substrate for functionalizing with carbon based molecules. The covalent binding to the surface can be through a bond between silicon and carbon, oxygen, nitrogen, sulfur, or other atom. In some embodiments the bond to the surface is between silicon and carbon. In some embodiments the bond to the surface is between silicon and oxygen.

Figure 4:
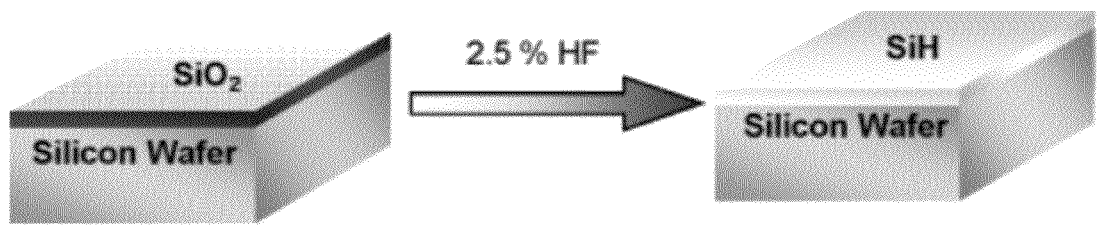
FIG. 4 illustrates a method of preparing of H-terminated silicon surface (Si—H).

In some embodiments, the immobilization of the redox active moiety by covalent binding to the silicon surface is accomplished by reaction with a silicon hydride (Si—H) surface. A silicon hydride surface can be obtained, for example by treatment of the silicon surface, for example a surface that is in the native oxide state, with hydrofluoric acid (HF). For example, dilute (1-3%) aqueous HF treatment, or, a 40% aqueous $NH_4F$ treatment can be used to create a Si—H terminated surface. Porous silicon, when etched through standard procedures involving HF, can also be used as a Si—H surface. FIG. 4 shows a schematic illustrating the conversion of a native oxide surface to a Si—H surface on a silicon wafer through the treatment of the wafer with a 2.5% aqueous solution of HF. A Si—H surface can also be formed by other processes, for example by decomposition of silanes as described in U.S. Pat. No. 6,444,326. A Si—H surface can also be formed through reacting surface silanol moieties with reagents such as trihydroxyhydridosilane via sol-gel type methods (see e.g. U.S. Pat. No. 5,017,540, and U.S. Pat. No. 5,326,738).

The Si—H surface can be reacted with a variety of functional groups to create covalent bonds and thereby attach a redox active moiety to the silicon surface. The Si—H surface can participate in hydrosilylation reactions, involving the addition of the Si—H across an unsaturated site to form a Si—C, Si—O, or Si—N bond to the surface. Functional groups which can be used in hydrosilylation include alkenes, alkynes, imines, carbonyls and oximes. Hydrosilylation can be carried out thermally, photochemically, with a metal catalyst or with a radical initiator (see Buriak, Chem Commun, 1999, 1051-1060). The Si—H surface can also be reacted with alkyl or aryl carbanions through, for example, Grignard, or lithium reagents. In some embodiments, the Si—H surface can react with azido, diazo, and diazonium groups.

FIG. 5 illustrates the reaction of a surface Si—H with an aldehyde functionality attached to a ferrocene redox active moiety to create a covalently bound ferrocene through a Si—O bond. FIG. 5 also illustrates the reaction of a surface Si—H with a vinyl functional group attached to a ferrocene redox active moiety to create a covalently bound ferrocene through a Si—C bond. FIG. 6 illustrates the reaction of a surface Si—H with an aldehyde functionality attached to an anthracene redox active moiety to create a covalently bound anthracene through a Si—O bond. FIG. 6 also illustrates the reaction of a surface Si—H with a vinyl functional group attached to an anthracene redox active moiety to create a covalently bound anthracene through a Si—C bond. FIG. 7 illustrates the reaction of both a ferrocene redox active moiety and an anthracene redox active moiety through vinyl functionality to produce a silicon surface with a covalently attached redox group that is sensitive to hydrogen ion (anthracene) and a covalently attached redox group that is insensitive to hydrogen ion (ferrocene). In some embodiments, a carbonyl group such as an aldehyde group is substituted for the vinyl functionality for providing attachment to the surface.

The redox active moieties can alternatively be attached covalently to the surface by direct reactions with a silicon surface from which all functionality has been removed, usually by high temperature and vacuum. The pure silicon surface can react directly, for example with alkenes and alkynes to form Si—C covalent attachment. (see Bateman, et. al., *Angew. Chem. Int. Ed.* 1998, 37(19), 2683-2685). Diazonium species can also be used to functionalize the surface either thermally or electrochemically. In some embodiments, ultrahigh vacuum techniques can be used to prepare the functionalized surfaces of the invention, for example by [2+2] Reactions of alkynes and alkenes or Diels-Alder ([4+2]) reactions of dienes with reconstructed Si surfaces.

Capping of silica and glass surfaces with alkyl-, alkoxy- and chloro-silanes may also be used to functionalize the silicon surface.

The silicon surface often contains oxide functionality including hydroxy functionality (native oxide). In some embodiments, the silicon electrodes of the invention are modified by covalent attachment to this oxide functionality. The hydroxy groups of silicon can often be coupled to surface bound groups using the many reactions known in organic chemistry for carbon bound hydroxy groups, including for example, the formation of esters and ethers. One derivatization method involves the use of a carbodiimide for coupling to the surface. Exemplary carbodiimides include, for example, dicyclohexylcarbodiimide (DCC), or (1-ethyl-3-[3-dimethylaminopropyl]carbodiimide Hydrochloride) (EDC).

The redox active moieties can also be attached covalently to the surface by reactions with the native oxide, Si—O or Si—OH on the silicon surface. Many methods are known for carrying such reactions to form covalent bonds through various functional groups (see Maoz et al., *J. Colloid. Interface Sci.*, 1984, 100, 465-496). In some embodiments an indirect approach can be employed in which an alkoxysilane comprising other reactive functionality is reacted with the Si—O or Si—OH groups on the surface to covalently attach the alkoxysilane to the silicon surface. The other reactive functionality on the alkoxysilane can then be used to covalently attach a redox active moiety to the surface. In these embodiments, the alkoxysilane can become a linker or portion of a linker. The other reactive functionality can be any reactive functionality that can be used to attach a redox active moiety. The functionality can be, for example, an olefin, an amine, or an epoxy group. The reaction used to couple the alkoxysilane to the redox active moiety can be, for example, a Diels-Alder reaction, a Michael addition, click chemistry, or epoxy chemistry.

In some embodiments, the reactions described above for covalently attaching functional groups to the silicon surface are used to attach a linker group or portion of a linker group having a chemical functionality that can be used to covalently bind the redox active moiety to the surface in a subsequent step.

Reactions that can be used to covalently attach a redox active moiety to the silicon surface include hydrosilylation, free radical reactions, carbodiimide coupling, Diels-Alder reactions, Michael addition, or click chemistry (see, e.g. Evans et al. *Australian Journal of Chemistry* 60 (6): 384-395 (2007).

In some cases the surface of the silicon is modified by coating the surface with conductive compounds such as metals or metal oxides. In some embodiments, the silicon is coated with gold, silver, palladium, copper, platinum or other metals. The metals can be coated from solution, for example by electrodeposition, or can be coated onto the surface with vacuum techniques such as plasma deposition, or metal vaporization. The silicon surface can be coated with conductive metal oxide compounds such as indium-tin oxide. When these materials are coated onto the silicon electrode surface, the redox-active agents are attached to the silicon electrode by attachment to the layer on the silicon electrode.

Where a linker group is used, the liker can be small, for example one to 3 atoms, or can be longer, e.g. 20 to 100 atoms. The linker can also be any size between the small or longer linker. Where a short linker is used, the redox-active moiety is held close to the surface. Where a longer group is used, the redox active moiety may be able to move away from the surface, for example into the solution. Linker groups can comprise hydrophilic, hydrophobic groups, or mixtures thereof. Linker groups can comprise, for example, hydrocarbons, esters, ethers, amides, amines, carbonyls, thiols, olefins, silicones, or other organic, inorganic or organometallic groups. The linker groups can be formed by polymerization or oligomerization reactions such as free radical or anionic polymerization. The linker group can comprise, for example, ethylene oxide, propylene oxide, or acrylamide repeat units. Linkers can have ring structures including aromatic rings.

The variation in the linker structure can be used to vary the mobility of the redox-active moiety in the solution.

A redox-active moiety may be highly substituted, and can still act as a redox-active moiety. Thus, for example, the redox-active moiety ferrocene includes substituted ferrocenes, ferrocene polymers, and ferrocene covalently attached to the surface via linker molecules.

In some embodiments, the redox-active moiety can be incorporated into a polymer, and the polymer comprising the redox active moiety can be immobilized onto the silicon surface. The immobilization of the polymer can be either chemical or physical. The immobilization of the polymer can be through covalent bonds, or through adsorption of the polymer to the silicon surface.

The redox active moieties can be incorporated into any type of polymer that can be immobilized onto the surface of the silicon surface. Types of polymers that the redox active moieties can be incorporated into include biopolymers such as RNA, DNA or proteins, conductive polymers, fluoropolymers, polyterpenes, inorganic polymers, phenolic resins polyanhydrides, polyesters, polyolefins, polysiloxanes, polyamides, polyimides, polyethers, polyketones, polysulfones, and vinyl polymers.

The polymer comprising the redox active moieties can, in some cases, be produced at the silicon surface. For example monomers or oligomers comprising the redox active moieties can be polymerized in the region of the surface to product the polymer near the surface. In some cases, the polymerization can be initiated at the polymer surface, resulting in polymer covalently bound to the surface. The polymerization can be initiated at the surface can be initiated, for example by a free radical reaction initiated by a diazo group attached to the silicon surface. In other cases, the polymerization can be initiated in solution, for example near the surface, such that the polymer which is formed is immobilized when it deposits onto the surface as it is formed. Methods for determining the appropriate solvent conditions are known. For example by establishing that the monomer and/or oligomer are soluble, while the polymer is insoluble, allowing for surface deposition to occur. The silicon surface can comprise polymerizable functional groups that are capable of copolymerizing with the monomers or oligomers comprising the redox active moieties resulting in covalently binding the redox active polymer onto the silicon surface.

In some embodiments, polymer comprising the redox active moieties can be electropolymerized at the silicon surface. For example, monomers comprising the redox active moieties are added to a solution, and current is provided through the silicon surface causing electropolymerisation of the monomers. In some embodiments, the electropolymerisation can result in the covalent attachment of the electropolymerized polymer to the silicon surface. In other embodiments, the electropolymerisation can result in polymerization in solution, and the polymer that is formed can deposit onto the silicon surface from the solution, resulting immobilization of the polymer by physisorption to the surface.

The polymers can be chemically or electrochemically deposited on individual microelectrodes, polymerized, as respond to a signal in a reversible manner, in a way that can be electrochemically detected. Other such materials are described by R. W. Murray in Electroanalytical Chemistry, vol. 13, edited by A. J. Bard (Marcel Dekker, NY 1984), the teachings of which are specifically incorporated herein.

In some embodiments, the polymer is formed away from the silicon surface, and subsequently immobilized thereto. The polymer can be immobilized onto the surface by a variety of methods including, adsorption from solution, coating including spin coating and dip coating, spraying, printing, electropainting, or electrodeposition.

In some embodiments the silicon electrode is formed by contacting an H-terminated silicon surface with the one or more redox-active moieties wherein at least one redox active moiety is sensitive to the presence of an analyte, wherein each redox-active moiety comprises a functional group that will react with the H-terminated silicon surface to form a covalently bond, thereby forming a derivatized silicon surface. In some embodiments, the surface comprises at least two redox active moieties and one of the redox active moieties is insensitive to the presence of the analyte Uses of the Compositions and Devices One aspect of the invention is a method of determining the concentration of an analyte. In one embodiment, the method comprises: placing an electrode in contact with said analyte, said electrode comprising a silicon substrate with silicon surface having immobilized thereon an analyte-sensitive redox-active moiety, said analyte-sensitive redox-active moiety exhibiting an oxidation potential and/or reduction potential that is sensitive to the concentration of the analyte; applying a plurality of potentials to the electrode; and measuring the current through the electrode at the plurality of potentials to determine a reduction and/or oxidation potential of the analyte-sensitive redox-active moiety, thereby determining the concentration of the analyte.

In one aspect the method comprises: determining the concentration of an analyte by (a) placing an electrode in contact with said analyte, said electrode comprising a silicon substrate with silicon surface having immobilized thereon an analyte-sensitive redox-active moiety, said analyte-sensitive redox-active moiety exhibiting an oxidation potential and/or reduction potential that is sensitive to the concentration of the analyte; (b) applying a plurality of potentials to the electrode; and (c) measuring the current through the electrode at the plurality of potentials to determine a reduction and/or oxidation potential of the analyte-sensitive redox-active moiety, thereby determining the concentration of the analyte.

The method of determining the concentration of the analyte can be used to measure pH by utilizing redox active moieties that are sensitive to hydrogen ion as described above.

The measurement of current at a plurality of potentials allows for carrying out voltammetry for determining the oxidation and or reduction potential of the redox active moiety or moieties immobilized on the surface. The voltammetry used in the method can be, for example cyclic voltammetry, pulse voltammetry, normal pulse voltamnaetry, square wave voltammetry, differential pulse voltammetry linear voltammetry, or square wave voltammetry. The source for supplying a plurality of potentials can be a potentiostat, for example, a potentiostat capable of applying square waves for square wave voltammetry.

The method often further comprises an analyte-insensitive redox-active moiety having a reduction and/or oxidation potential that is substantially insensitive to the analyte, further comprising determining the oxidation and/or reduction potential of the analyte-insensitive redox-active moiety, and determining the concentration of the analyte from the difference in the oxidation and/or reduction potentials of the analyte-sensitive and analyte-insensitive moieties.

Generally, the analyte concentration is determined by using voltammetry to identify the position of current peaks, which current peaks indicate the reduction or oxidation potential of a redox active moiety. In some embodiments, the position of the reduction and/or oxidation potential of the analyte sensitive redox active moiety is used to determine the concentration of the analyte. For example, the position of the current peak with respect to the potential at a reference electrode can be used. This method can be used, for example, where no analyte insensitive redox active moiety is employed.

Where an analyte insensitive redox active moiety is used, detection is generally accomplished by measuring the potential difference, delta E, associated with current peaks for oxidation (or reduction) of the immobilized redox active moieties, where the magnitude of delta E can be related to the concentration of analyte, e.g. hydrogen ion (H+) in solution. That is, in many embodiments, delta E represents the potential difference between the reduction and/or oxidation potential between a redox active analyte sensitive moiety and a redox active analyte insensitive redox active moiety. The analyte insensitive redox active moiety which has an electrochemical response that is insensitive to variations in the medium serves as the reference. Current peaks for oxidation or reduction of the reference and indicator can be determined from a voltammograms using a counter electrode, and without the need for a reference electrode.

The method calls using the measured current through the electrode at the plurality of potentials to determine the concentration of the analyte. The determination of the concentration using the measured current (e.g. current peaks) can be accomplished by using a computation system that communicates with the device for measuring current. The computation system can apply algorithms for calculating reduction or oxidation potential from the measured current at a plurality of potentials from the voltammetry measurements. The computing systems can be part of the sensing system, in some cases allowing the sensing system to be self contained. The computing system can utilize its memory for storing raw or processed data from the sensors. The method can further comprise communication between the computing system and the sensor via transmission device that will wirelessly or by wire transmit processed data to an external device.

Carrying out the method typically requires the use of at least one other electrode (the counter electrode). The counter electrode is needed to complete the electrochemical circuit in order to make the measurements described herein. The counter electrode is generally made of a material which is chemically inert to the medium so that its potential does not change significantly during the course of measurement. Suitable materials in many applications include platinum, gold, stainless steel, and carbon. In some cases, the counter electrode can be incorporated into the chip that also comprises the silicon sensor electrode.

A reference electrode is optional and is used as a third electrode in some embodiments of the method of measuring analyte concentration. In the case of a three-electrode system, the counter electrode generally completes the circuit, allowing current to flow through the cell, while the reference electrode maintains a constant interfacial potential difference regardless of the current. In the case where the system comprises an analyte sensitive redox active moiety and an analyte insensitive redox active moiety, the analyte insensitive redox active moiety can act as a reference, allowing the potential difference to be used to determine analyte concentration. Even where an analyte insensitive moiety, in some embodiments, a reference electrode will still be used. In some embodiments, pseudo-reference electrodes can also be utilized. Reference electrodes which can be employed are described above.

In many embodiments, the sample is a liquid sample, and the electrodes are each in contact with the liquid. In some cases, the sample will not be a liquid, but will be a solid, generally comprising a solid electrolyte, or a gas.

In some embodiments, the method involves the in-line sensing of a process. An in-line sensor can be a sensor that is used in an on-going process. In some embodiments the method comprise the use of a sensor is in a vessel, in other embodiments the sensor is in a conduit or pipe through which a process fluid flows. In some embodiments, the method comprises using currents measured at a plurality of potentials by voltammetry to determine analyte concentration, and the determined analyte concentration is used to control a process parameter. The systems of the present invention are valuable in in-line sensing in that they can be made to be robust, to resist fouling, and are able to measure analyte concentration for long periods of time in media that changes its properties, as in a process such as a chemical reaction, biochemical reaction, or fermentation.

One aspect of remote monitoring is that the sensor can be programmed to automatically take readings. The automatic readings could be programmed to occur on a periodic basis, to occur upon the happening of some event, or to occur when the sensor is prompted. The periodic events could be separated on the order of seconds to on the order of months. The happening of some event could be, for instance at the point when the measured solution reaches a certain volume level, or at given points in the steps of a manufacturing process (e.g. at the beginning of or end of a step, or upon the addition of a reagent to a vessel).

Remote monitoring generally includes communication from the remote sensing unit, and/or communication to the remote sensing unit. The communication to and from the remote sensing unit can be done with transmission lines, and/or wirelessly. Any type of signal including digital, analog, wideband, narrowband, etc. can be used.

One aspect of the present invention is the voltammetric monitoring of pH with a silicon electrode as part of process control in processes. In one embodiment, a voltammetric pH measurement is made in an industrial process stream, and the pH value from that measurement is used to as input to a decision on the adjustment a process parameter. In one embodiment, the pH value from the voltammetric pH measurement with a silicon electrode is used to decide whether or not to add one or more components to the process, and/or to decide how much of the component to add. In some embodiments, the pH value is used to control the pH in a part of the process, for example, as input into the decision on the addition of either acidic or basic components. In some embodiments, the pH value is used to determine whether a process has reached a certain stage, for instance, whether a reaction is at completion. In some embodiments, the pH value is used to determine the addition of nutrients or other components to a reaction containing an organism in order to maintain the health and productivity of the organism.

The process control step can be automated such that a given pH measurement value from the sensor results in the change of a process parameter without the intervention of a person. In other embodiments, the pH measurement is viewed by a person who uses the information to make the decision about the change of a process parameter.

The process control step can be controlled by a voltammetric pH system with a silicon electrode that has a sensor, a voltage source, a current measuring detector, and a computer for determining the pH from the current measurements. The voltammetric pH system can be in communication either with a process control system, or with an operator, by analog or digital means, either with a wire or by wireless connections.

One aspect of the invention is a method of voltammetric pH sensing with a silicon electrode wherein the pH sensor requires little calibration. In one aspect of the invention the pH sensor is substantially free of the need for calibration.

The use of the voltammetric pH sensing with a silicon electrode has a number of advantages. For example, the sensors of the present invention are solid-state sensors. The sensors of the present invention have a built-in internal standard such that calibration is not required. The sensors of the present invention can be constructed to be physically robust, such that they are not prone to breakage. The sensors of the present invention can be made to be relatively insensitive to fouling. The sensors of the invention can be constructed to be resistant to chemical sterilization such as exposure to ethylene oxide, UV stabilization, gamma irradiation, electron beam irradiation, and temperature treatment. The sensors of the invention can be constructed to be resistant to high humidity and high temperature treatment under pressure such as experienced in an autoclave.

The voltammetric pH sensing methods with a silicon electrodes comprise reactions carried out in stainless steel reactors, glass reactors (e.g. for product development), and disposable reactors (e.g. plastic reagent bags), for example reactors described by manufacturers such as Wave Biotech, Hyclone, Xcellerex, and Stedim.

One aspect of the invention involves methods of voltammetric pH sensing with a silicon electrode for downstream processing including chromatography and tangential flow ultrafiltration.

Another aspect of the invention is as a sensor in a remote monitoring systems such as a drug (pharmaceutical agent) delivery system. Such a system is described, for example, in U.S. Patent Application 2003/0153900. The analyte monitoring system or monitoring and drug (pharmaceutical agent) delivery system can be partitioned into a disposable module, a reusable module and a PDA module. This configuration optimally distributes functionality among these three configurations to achieve certain advantages. However the invention is not limited to this configuration. For example, a one-unit disposable device including all electronics, microneedles, chemistry, sensors, mechanics and user interface may be alternatively employed. Or, more relevantly, the design of the invention allows for any distribution of components between one or more system modules. For example, components may be partitioned among one or more system modules based on the overall system cost, user safety and/or performance concerns.

The disposable module contains those components that once used must be discarded to maintain safety and accuracy. This module preferably includes any structural or mechanical elements to maintain integrity, sterility and/or an electromechanical interface to any reusable components. Therefore this system module can include, for example: microneedles, a microfluidic assembly, membrane, reagent chemistry and associate housing materials. The portion of a sensor which is in contact with a biological fluid, for example, may be part of the disposable module. This module can also include retaining mechanisms for establishing and maintaining intimate contact with the body thereby providing mechanical retention of the analyte monitoring/drug (pharmaceutical agent) delivery system.

The reusable module generally contains those components that control, automate motion, measure the analyte concentration, alarm the user, transmit data to the PDA module. This module can also include retaining mechanisms. Generally, this module includes: a microprocessor with associated circuitry (e.g., memory, supporting electronics and the like), sensing circuitry, including, for example, a voltage supply and current measuring device, drive mechanisms such as motors or the like, a power supply (e.g., battery) and an interface operable to communicate with a portable computing device or PDA. The interface can be RF, magnetic or inductive, optical or the like. The reusable module can also an audible or vibration alarm to notify the user that user action intervention is required.

The PDA module generally includes a separate user interface via a portable computing device such as a personal digital assistant (PDA), handheld computer or the like for controlling and/or interacting with the device. A typical portable computing device includes a processor, memory, associated circuitry, a display (e.g., monochrome or color LCD) and an input device such as a key pad, touch screen (e.g., integrated with the display) or the like and an operating system. The display can show the value of the analyte to be measured, could provide the user with instructions on how to respond to the measured level of analyte, or may tell the user what automatic actions have been taken in response to a measured level of analyte.

Today, portable computing devices with improved operating system software and user interfaces are readily available. These devices provide the potential for rich and extended functionality. For example a typical PDA includes a relatively large viewing screen and can also include wireless communications mechanisms, a sophisticated operating system and a variety of business and personal software (calendars, scheduling, etc.). The invention preferably includes the use of a PDA to provide the proprietary software (programs) for autonomous operation with an improved user interface.

For example, the PDA module can provide the user with software that facilitates informed decisions to help a patient user more optimally adjust either drug or dietary consumption to more optimal levels. The PDA configuration provides a user interface and preferably allows users the ability to program and or control testing. The user can view individual glucose measurements and graphically display analyte level trends by the day, week or custom time period. The PDA can be used to display any and all of the measurements recorded by the system. Using the proper software, the user can be provided with recommendations for drug regiment modification. In some cases, the user can program the times when their analyte tests are to be taken. Preferably, the user can also set the upper and lower limits for alerts.

The system can be programmed such that whenever a user makes changes and with verification from the user, the information can be wirelessly downloaded to the system. During the day the user may not need to use the PDA unless alerted by the system to check for an analyte reading. The user can initiate a test from the PDA if wanting to make an immediate measurement. Once the user selects this command, verifies it, and transmits it to the reusable module, a confirmation is made back to the PDA.

In one aspect the invention comprises drug dispenser capsule comprising a voltammetric sensor. In some embodiments, the drug dispenser capsule comprises a silicon based voltammetric sensor as described herein. The drug dispenser capsule of the present invention internally senses a biologic condition by the detection of the presence or amount of an analyte, and internally dispenses drugs within the digestive tract of a body (e.g., a human body or animal body) based upon the sensed level of analyte. The capsule is inert and is therefore swallowable and passable through the digestive tract without being consumed. By sensing the level of one or more analytes, the swallowable drug dispenser capsule senses information about the digestive tract or senses conditions within the digestive tract that are indicative of conditions in other organs (e.g., skin). In addition to the voltammetric analyte sensor, the capsule contains one or more other sensors (e.g. chemical, electrical, etc.) so that more types of biologic data can be tracked through the digestive system. In response to that sensed information, the capsule dispenses a bioactive substance within the digestive tract without the need to transmit or receive signals from a remote transmitter/receiver, and without active human or computer management. Drug dispenser capsules are described, for example, in U.S. Pat. No. 6,929,636.

The swallowable drug dispensing capsule comprising a voltammetric sensor can include, for example, sensors, a controller, memory, optional programmable logic, a power supply, a microactuator, a drug storage module, and communication interface having at least one of the following types of communication modules: radiofrequency; ultrasonic; and/or infrared. In one preferred embodiment, at least memory, and preferably also controller and/or programmable logic are embodied on a silicon-based module in one or more semiconductor chips.

In some embodiments, the swallowable drug dispensing capsule has multiple sensors that are arranged about an outer surface of capsule in a desired predetermined orientation that is expected to expose each sensor to a targeted bodily condition or landmark within the human body. Each sensor can comprise a single type of sensor such as an image detector or a different type of sensor (e.g. chemical, electrical, temperature, etc.). Chemical detectors detect the presence of many analytes, such as pH, or the concentration of glucose, which is relevant to treatment of diabetes patients.

The swallowable drug dispensing capsule of the invention can have a controller that regulates communication between sensors and memory, communication between memory and any remote controllers outside of the human body, and communication with programmable logic component(s). Finally, controller can operably control both communication interface and a microactuator. The controller typically is a logic controller and includes a microprocessor. The controller may also comprise one or more logical devices (e.g., a logic gate) capable of performing a sequence of logical operations.

The swallowable drug dispensing capsule generally has a memory or storage device that is typically an ultra-high capacity storage device, and which is often based on a silicon chip. In one embodiment, the memory is an atomic resolution (ARS) storage device capable of storing a large volume of data, such as megabytes to gigabytes of data points, within a relatively small storage area. The atomic resolution storage device is a low power consumption storage device, and may require less than 500 mW to operate. In one preferred embodiment, ARS module can have a size of about 1 square millimeter, suitable to be carried within a swallowable medical capsule. In addition, ARS module can include its own modules that correspond to the functions of programmable logic and/or controller. Other subminiature memory devices, known to those skilled in the art, that have a high storage capacity with relatively low power consumption can be used in place of an ARS module. One atomic resolution storage device suitable for use in the swallowable data recorder capsule medical device according to the present invention is disclosed in U.S. Pat. No. 5,557,596.

The swallowable drug dispensing capsule generally has a drug storage module and a microactuator. The drug storage module represents a container for holding a drug or bioactive substance that will be released, for example, into the digestive tract. Accordingly, the drug storage module also includes one or more selectively activated dispensing ports that open in an outer surface of capsule. The microactuator can have a chemically activated or electromechanically activated mechanism for causing the drug storage module to release its contents. The swallowable drug dispensing capsule has a suitable power supply, such as a lithium-ion battery, which is relatively non-toxic. Alternatively, the power supply can be a disposable, chemically-based battery, which generally is an encapsulated removable module that can be replaced as needed. Other power supplies known to those skilled in the art that is suitable for in vivo environments can be used.

The swallowable drug dispensing capsule generally has a communication interface that includes any suitable wireless transmission technology (e.g. ultrasonic, radiofrequency, etc.) that readily permits communication to and from the capsule while the capsule is in digestive tract and the remote transmitter/receiver which is located remotely outside of the body. However, an infrared port is preferably used for communicating with capsule after capsule is captured from the body. Likewise, an infrared port may be used for programming the controller, memory, and/or logic component prior to insertion of capsule within the body to determine the manner in which the sensors will operate and communicate with the memory, as well as the manner in which microactuator will operate and communicate with memory via controller.

In use, the sensors, including the voltammetric sensor of the capsule sense analyte concentrations and biologic data within the digestive tract and the sensed data is passed through the controller for storage in memory and/or comparison with a stored data profile in memory and/or logic. After the predetermined criteria are met, controller activates microactuator to dispense the drug from drug storage module into digestive tract. The sensed data optionally is stored in memory and retrieved via the communication interface after capture of capsule upon exiting the digestive tract. Finally, a wireless communication system optionally can be used in addition to, or as an alternative to, controller and memory to facilitate evaluating and storing sensed data and to dispense drugs upon selective activation at the appropriate time.

The silicon electrode voltammetric pH sensors of the present invention can be used in manufacturing operations such as the manufacture of coatings, cleaners and sealers that enhance paint and finish bonding, metal passivation to protect substrates during shipment and storage, paint spray booth treatments that enhance quality and efficiency, and air scrubbers that limit pollutant emissions. In these applications, the reliable measurement of pH can be an integral part of the process.

In one aspect the sensors of the present invention can be used as embeddable corrosion measuring instrument that is capable of providing information related to corrosion rate, corrosion potential, conductivity and chloride concentration, and pH levels of steel rebar reinforced structures. The devices can be used to monitor the integrity of the steel. The devices and systems of the present invention do not require a direct electrical connection to the reinforcement steel within the structure, using the structural steel as one of the referencing materials. Since the disclosed instruments do not require proximity to the steel within the structure, the instruments can be dispersed at critical locations within the structure, regardless of steel placement. In some embodiments, the systems and devices are self-contained, incorporating all required sensing electrodes and electronics. The devices can be deployed as described in U.S. Pat. No. 6,690,182.

The silicon electrode voltammetric pH sensors of the present invention can be used in winemaking. Measurements of various properties including pH are taken throughout the process, including during (1) pressing, (2) primary fermentation, which often takes between one and two weeks, where yeast converts most of the sugars in the grape juice into ethanol (alcohol) (3) secondary fermentation.

The silicon electrode voltammetric pH sensors of the present invention can be used in brewing. The measurement of pH can be important at the various stages of brewing, for example, at mashing, lautering, lauter tun, mash filter, boiling, whirlpool, wort cooling, fermenting, conditioning, filtering, and secondary fermentation. The silicon electrode voltammetric pH sensors of the present invention can be particularly important during fermentation, where the voltammetric pH sensors of the present invention are advantageous as they require little to no calibration, and can be made to resist fouling during the fermentation process.

The silicon electrode voltammetric pH sensors of the present invention can be used in the production of biofuels, including the production of biodiesel, ethanol, butanol, and substitutes for gasoline, diesel, jet fuel, and additives to be used in any of the forgoing. The production of ethanol includes both the process of converting the cellulose to sugars, and the process of converting the sugars to ethanol. Although there are several key technological differences in how ethanol is produced from corn or cellulosic feedstock, both paths to ethanol production require a fermentation step that involves the conversion of glucose and other sugars to ethanol. Currently, baker's yeast, *Saccharomyces cerevisiae*, provides the primary microbiological system used by the corn-based ethanol industry. The methods of the present invention relate to ethanol production for fuel from *Saccharomyces cerevisiae* and other organisms.

The silicon electrode voltammetric pH sensors of the present invention can be used in oil recovery and refining. The sensors can be incorporated into down-hole devices for measuring the analytes present in the down-hole environment. The sensors can be used in other aspects of processing the oil such as in oil refining.

The silicon electrode voltammetric pH sensors of the present invention can be used in the production of biopharmaceuticals, for example, medical drugs produced using biotechnology. They include, for example, proteins (including antibodies), nucleic acids (DNA, RNA or antisense oligonucleotides) used for therapeutic or in vivo diagnostic purposes. Biopharmaceuticals are produced by means other than direct extraction from a native (non-engineered) biological source. An example is recombinant human insulin (rHI, trade name Humulin), which was developed by Genentech and marketed by Eli Lilly.

An aspect of the invention is a silicon electrode voltammetric pH sensor for the production of biopharmaceuticals including: blood factors (e.g. Factor VIII and Factor IX), thrombolytic agents (e.g. tissue plasminogen activator), hormones (e.g. insulin, growth hormone, gonadotropins), haematopoietic growth factors (e.g. erythropoietin, colony stimulating factors), interferons (e.g. interferons-α, -β, -γ), interleukin-based products (e.g. interleukin-2), vaccines (Hepatitis B surface antigen), monoclonal antibodies (e.g. infliximab, basiliximab, abciximab, daclizumab, gemtuzamab, alemtuzumab, rituximab, palivizumab, trastuzumab (perception), and etanercept) and other products such as tumor necrosis factor, and therapeutic enzymes.

One aspect of the invention is a method of making a protein comprising carrying out a fermentation reaction that produces such protein wherein the pH of the fermentation is controlled by measuring the pH with a pH sensor comprising a silicon surface having immobilized thereon a redox active moiety that is sensitive to the presence of hydrogen ion, and using the measured pH to control the pH of the fermentation reaction. In some embodiments, the control of the pH can be manual, for instance, where an operator reads the pH from the pH sensor and uses the measured pH in order to determine whether or how much to adjust the pH, and in other embodiments, the control can be automatic, where the pH measurement is read by instruments that can adjust the pH based on the value of the measurement received.

Many biopharmaceutical products are pharmaceuticals that are derived from life forms. Small molecule drugs are not typically regarded as biopharmaceutical in nature by the industry.

The silicon electrode voltammetric pH sensors of the present invention can be used for biopharmaceuticals produced from microbial cells (e.g. recombinant E. coli), mammalian cell lines and plant cell cultures in bioreactors of various configurations.

Cell culture requires cells to be grown, often under a strict set of conditions in order to maintain the health of the cells and maximize the production of the culture. Cells are grown and maintained at an appropriate temperature and gas mixture (for example, 37° C., 5% CO2) in a cell incubator. Culture conditions vary widely for each cell type, and variation of conditions for a particular cell type can result in different phenotypes being expressed.

Aside from temperature and gas mixture, the most commonly varied factor in culture systems is the growth medium. Recipes for growth media can vary in pH, glucose concentration, growth factors, and the presence of other nutrient components. The effect of changes in pH can be dramatic in some cases, and it can be important to maintain the pH. The devices, systems, and methods of the invention allow for control of pH within a range of 1, 0.5, 0.02, 0.1, 0.05, 0.02, 0.01 pH units or less in order to maintain the growth and health of the cells. The silicon electrodes of the present invention allow for the accurate measurement of pH with limited fouling, and in some embodiments, no need for calibration.

The silicon electrode voltammetric pH sensors of the present invention can be used for cells that are grown completely in solution, and for cells that are grown on a substrate. Some cells naturally live without attaching to a surface, such as cells that exist in the bloodstream. Others require a surface, such as most cells derived from solid tissues. Cells grown unattached to a surface are referred to as suspension cultures. Other adherent cultures cells can be grown on tissue culture plastic, which may be coated with extracellular matrix components (e.g. collagen or fibronectin) to increase its adhesion properties and provide other signals needed for growth.

Figure 17:
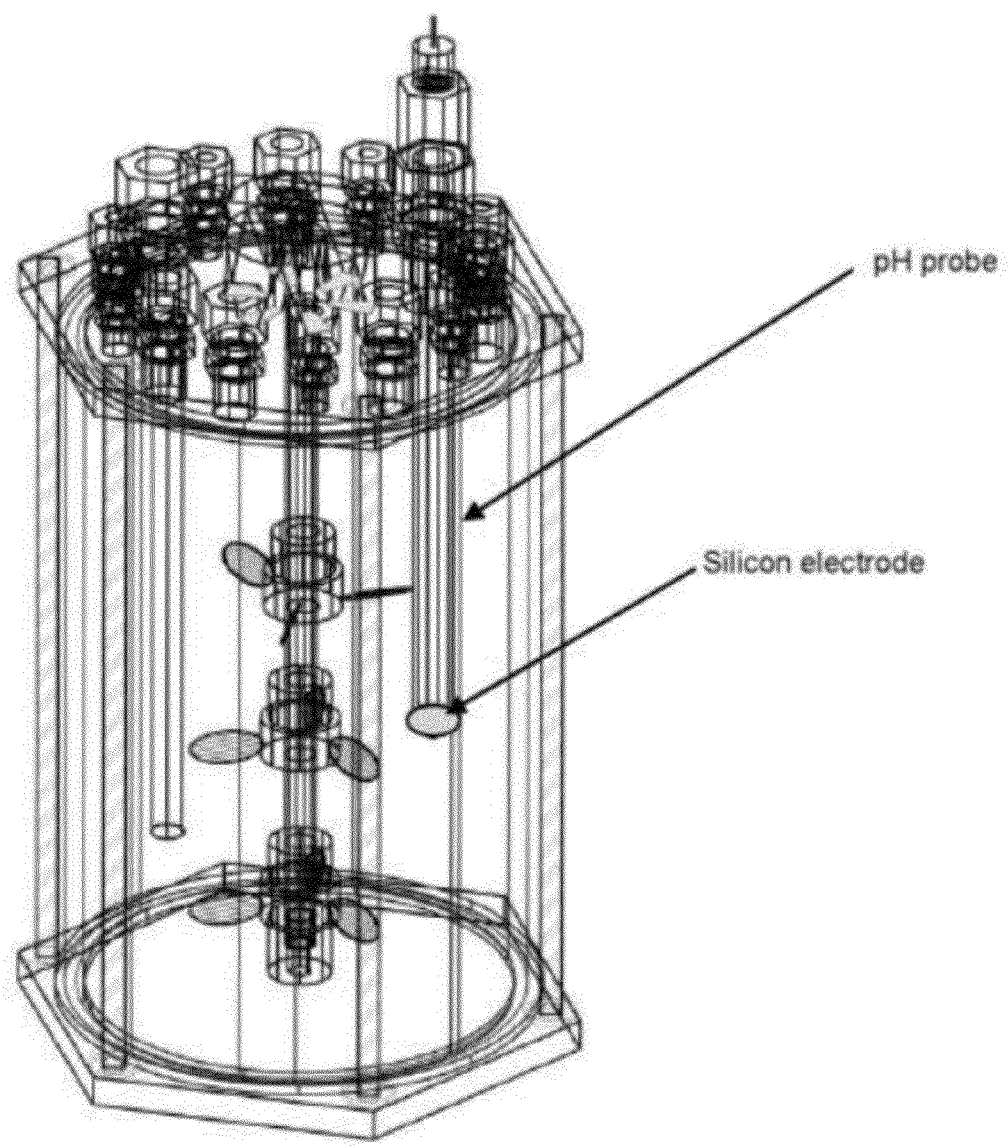
FIG. 17 is a drawing of an embodiment of a bioreactor of the invention comprising a silicon-based voltammetric sensor.

One aspect of the invention is a bioreactor or fermentor in which the reaction or fermentation occurring therein is controlled by a silicon based voltammetric sensor of the invention. In one embodiment, the invention comprises a bioreactor comprising a silicon based sensor wherein the silicon sensor comprises a silicon surface having immobilized thereon a redox active moiety that is sensitive to the presence of an analyte, such as hydrogen ion. FIG. 17 shows an example of a bioreactor of the invention comprising a probe for measuring pH, and thereby controlling the pH in the reactor during the reaction. The probe comprises an electrode having a silicon surface having immobilized thereon a redox active moiety that is sensitive to hydrogen ion. In some embodiments the probe comprises two electrodes, each comprising a silicon surface, one of the electrodes having immobilized thereto a redox active moiety that is sensitive to hydrogen ion, and one of the electrodes having attached thereto a redox active moiety that is insensitive to hydrogen ion. In some embodiments the probe further comprises a counter electrode, and in some embodiments it further comprises a reference electrode.

The silicon electrode voltammetric pH sensors of the present invention can be used to assist in the successful manipulation of cultured cells. As cells generally continue to divide in culture, they generally grow to fill the available area or volume. This can generate several issues that the reliable measurement of pH can assist with, such as: Nutrient depletion in the growth media; accumulation of apoptotic/necrotic (dead) cells; cell-to-cell contact stimulating cell cycle arrest, causing cells to stop dividing known as contact inhibition; cell-to-cell contact stimulating promiscuous and unwanted cellular differentiation Sometimes these issues can be identified by monitoring pH, alone or in combination with other measurements, and can then be controlled or remedied by adjusting tissue culture conditions which often rely on sterile techniques. These methods aim to avoid contamination with bacteria or yeast that will compete with mammalian cells for nutrients and/or cause cell infection and cell death. The pH measurements of the present invention are amenable to being carried out in a biosafety hood or laminar flow cabinet to exclude contaminating micro-organisms.

The silicon electrode voltammetric pH sensors of the present invention can be used for pH sensing in plant tissue culture, bacterial and yeast cell culture, and viral cell culture.

An aspect of the invention is a silicon electrode voltammetric pH sensor for sensing pH in plant tissue culture. The pH measurements of the present invention can be used at any step of plant cell culture. Plant tissue culture is typically performed under aseptic conditions under filtered air. Living plant materials from the environment are naturally contaminated on their surfaces (and sometimes interiors) with micro-organisms, so surface sterilization of starting materials (explants) in chemical solutions (usually alcohol and mercuric chloride) is an important first step. Explants are then usually placed on the surface of a solid culture medium, but are sometimes placed directly into a liquid medium, particularly when cell suspension cultures are desired. Solid and liquid media are generally composed of inorganic salts plus a few organic nutrients, vitamins and plant hormones. Solid media are prepared from liquid media with the addition of a gelling agent, usually purified agar. The pH measurements of the present invention can be made in the liquid in the moist soil, or in the agar. The composition of the medium, particularly the plant hormones and the nitrogen source (nitrate versus ammonium salts or amino acids), and the pH, can have profound effects on the morphology of the tissues that grow from the initial explant. For example, an excess of auxin will often result in a proliferation of roots, while an excess of cytokinin may yield shoots.

The silicon electrode voltammetric pH sensors of the present invention can be used with any cell line including: National Cancer Institute's cancer cell lines, zebrafish ZF4 and AB9 cells, Madin-Darby Canine Kidney MDCK epithelial cell line, Chinese Hamster Ovary CHO cells, Insect cell line Sf21, MCF-7 (breast cancer), MDA-MB-438 (breast cancer), U87 (glioblastoma), A172 (glioma), HeLa (cervical cancer), HL60 (promyelocytic leukemia), A549 (lung cancer), HEK 293 cells (kidney-original HEK line is contaminated with HeLa), SHSY5Y Human neuroblastoma cells, cloned from a myeloma, Jurkat cell line, derived from a patient with T cell leukemia, BCP-1 cells (PEL), Primate cell lines, Vero (African green monkey Chlorocebus kidney epithelial cell line initiated 1962), COS-7 (African Green Monkey Kidney Cells), Rat tumor cell lines, GH3 (pituitary tumor), 9L (glioblastoma), Mouse cell lines, 3T3 cells, MC3T3 (embryonic calvarial), C3H-10T1/2 (embryonic mesenchymal), NIH-3T3 (embryonic fibroblast), Invertebrate cell lines, C6/36 *Aedes albopictus* (Asian tiger mosquito) larva, Plant cell lines, Tobaco BY-2 cells (kept as cell suspension culture, they are model system of plant cell).

An aspect of the invention is a silicon electrode voltammetric pH sensor for use in water purification. Water purification is the process of removing contaminants from a raw water source, the goal is generally to produce water for a specific purpose with a treatment profile designed to limit the inclusion of specific materials. Water purification is not only water purified for human consumption or drinking water. The silicon electrode voltammetric pH sensors of the present invention can also be used water purified to meet the requirements of medical, pharmacology, chemical and industrial applications. The silicon electrode voltammetric pH sensors of the present invention can be used in water purification processes including, but not limited to ultra violet light; filtration; softened water; reverse osmosis, ultrafiltration; molecular stripping; deionization; and carbon treatment. Water purification may remove particulate sand, suspended particles of organic material; parasites, such as *giardia*; cryptosporidium; bacteria; algae; virus; fungi, etc; minerals such as calcium, silica, magnesium; and toxic metals such as lead, copper; and chrome. Some purification may be elective in its inclusion in the purification process; examples, smell (hydrogen sulfide remediation), taste (mineral extraction), and appearance (iron encapsulation).

Water from any source is applicable to the present invention. While groundwater (well water) is a more economical choice for drinking water, as it is inherently pre-filtered, by the aquifer from which it is extracted. Water from an aquifer will have a limited output and can take thousands of years to recharge. Surface water; (rivers, lakes, streams) is far more abundant and is the typical raw water source used to make drinking water, as a water source it is carefully monitored for the presence of a variety of contaminants. The methods of the present invention encompass the voltammetric measurement of pH of these types of water where the pH value of the measurement can be used to decide on the purity of the water.

The silicon electrode voltammetric pH sensors of the present invention can be used with water purification methods including: pumping and containment, screening, storage, preconditioning, pre-chlorination, and removal of the fine solids, micro-organisms and some dissolved inorganic and organic materials.

Distilled water generally has an average pH of about 7 (neither alkaline or acidic) and sea water generally has an average pH of 8.3 (slightly alkaline). If the water is acidic (lower than 7), lime or soda ash can be added to raise the pH. Lime is the more common of the two additives because it is cheaper, but it also adds to the resulting water hardness. Neutralizing with soda ash, however, increases the sodium content of the water. Making the water slightly alkaline can ensure that coagulation and flocculation processes work effectively and also helps to minimize the risk of lead being dissolved from lead pipes and lead solder in pipe fittings. The pH value can be used to determine whether water is hard or soft. In general, water with a low pH (<6.5) could be acidic, soft, and corrosive. Therefore, the water could contain metal ions such as iron, manganese, copper, lead, and zinc . . . or, on other words, elevated levels of toxic metals. This can cause premature damage to metal piping, and have associated aesthetic problems such as a metallic or sour taste, staining of laundry, and the characteristic "blue-green" staining of sinks and drains. More importantly, there are health risks associated with these ions or contaminants. The primary way to treat the problem of low pH water is with the use of a neutralizer. The neutralizer feeds a solution into the water to prevent the water from reacting with the household plumbing or contributing to electrolytic corrosion. Water with a pH>8.5 could indicate that the water is hard. Hard water does not pose a health risk, but can cause aesthetic problems. These problems include an alkali taste to the water formation of a deposit on dishes, utensils, and laundry basins, difficulty in getting soaps and detergents to lather, and formation of insoluble precipitates on clothing.

Another aspect of the invention is sensing of analyte levels such at the pH of bodies of water for example for resource control. The body of water can be, for example, a lake, ocean, stream, or river. The ability of the invention to be used remotely and to be used without the need for frequent calibration or any calibration at all allows the systems, devices, and electrodes to be deployed remotely in bodies of water to provide information on analytes such as hydrogen ion, etc. in such remote bodies.

An aspect of the invention is a silicon electrode voltammetric pH sensor for the measurement of pH in processes related to sewage treatment. Sewage treatment can have the same steps as described above, but may refer to water that has a higher level of contamination. Raw influent (sewage) can be the liquid waste from toilets, baths, showers, kitchens, sinks etc. Household waste that is disposed of via sewers can compose the sewage. In some areas sewage also includes some liquid waste from industry and commerce.

The pH sensors of the present invention are suitable for single use, or for disposable applications.

The pH sensors of the present invention are amenable to miniaturization.

EXAMPLES

Reagents and Instrumentations

Vinylferrocene, vinylanthracene, hydrofluoric acid were purchased from Sigma-Aldrich (Sigma-Aldrich INC., USA), ferrocenecarboxaldehyde and mesitylene were obtained from Alfa Aesar (Alfa Aesar INC., USA), and 9-anthracene-carboxaldehyde was obtained from Acros Organics (Acros Organics INC. USA). All the chemicals were obtained with the highest grade available and were used without further purification.

Different single-side polished, primary flat, 500 µm thick silicon wafers with (111) and (100) orientation were purchased from Virginia Semiconductor with the following specification: i) p-type (100, 10-90$\Omega$ cm resistivity), ii) p-type (100, 0.001-0.005$\Omega$ cm resistivity), iii) n-type (100, 10-40$\Omega$ cm resistivity), iv) n-type (100, 0.02-0.05$\Omega$ cm resistivity), v) p-type (111, 0.001-0.004$\Omega$ cm resistivity) and vi) n-type (111, 0.001-0.005$\Omega$ cm resistivity).

Electrochemical measurements were recorded using an Autolab computer controlled potentiostat (Ecochemie, Utrecht, Netherlands) with a standard three-electrode configuration, consisting of a saturated calomel reference electrode (SCE, Radiometer, Copenhagen, Denmark), a platinum auxiliary electrode (Bioanalytical Systems INC., USA)) and silicon (Virginia Semiconductor INC, USA) working electrode.

Different pH solutions in the range of 1 to 12 were also prepared in deionised water as follows: pH 1.2, 0.10 M perchloric acid; pH 2.2, 0.05 M perchloric acid; pH 4.6, 0.1 M acetic acid+0.10 M sodium acetate; pH 5.6, 0.5 M sodium acetate; pH 6.5, 0.025 M $K_2PO_4$+0.025 M $KH_2PO_4$; pH 7.33, 0.05 M $K_2PO_4$; pH 9.3, 0.10 M sodium borate; pH 13.5, 0.1 M sodium hydroxide. These solutions also contained an addition of 0.10 M sodium perchlorate as supporting electrolyte. The pH of these solutions was measured using the SevinMulti (Mettler Toledo) pH meter.

Example 1

Preparation of H-Terminated Silicon Surface

Silicon wafers (oriented (111) or (100), cut into ca. 1×1 cm$^2$ pieces) were cleaned using "Piranha" solution (concentrated $H_2SO_4$:30% $H_2O_2$, 3:1, v/v) at about 80° C. for 30 min and rinsed thoroughly with deionized water. Subsequently, the wafer pieces were oxidized in $H_2O_2$:HCl:$H_2O$ (2:1:8) at about 80° C. for 15 min, and in $H_2O_2$:$NH_4OH$:$H_2O$ (2:1:8) at about 80° C. for another 15 min, rinsed copiously with deionized water. The cleaned Si(100) wafers pieces were then etched in 2.5% HF solution for about 15 min. These procedures eliminate the native oxide layer of Si, yielding an H-terminated surface. The H-terminated substrates were quickly rinsed with deionized water, dried with nitrogen gas and were used immediately for the derivatization experiments. The Si(100) (10-90Ω cm, p-type) was used for the experiments below.

Example 2

Derivatization of H-Terminated Silicon Surface with Ferrocene Moieties

Approximately 10 mmol mesitylene solution of vinylferrocene (VFc) or ferrocenecarboxaldehyde (FcA) was put in a round bottom flask and bubbled with nitrogen or argon gas for at least 30 min. A piece of the H-terminated silicon substrate was then immersed in the solution and allowed to react with VFc or FcA for about 12 h under reflux at about 150° C. in an oil bath. During the reaction, the solution was also purged with nitrogen (or argon) to eliminate dissolved oxygen and to prevent the substrate from being oxidized. After the reaction, the substrate derivatized with VFc or FcA was rinsed with dichloromethane, acetonitrile and methanol, and dried under a stream of nitrogen gas. The derivatization of the H-terminated surface with ferrocene moieties as described in Example 2 is illustrated in FIG. 5.

Example 3

Derivatization of H-Terminated Silicon Surface with Anthracene Moieties

Approximately 10 mmol mesitylene solution of vinylanthracene (VA) or anthraldehyde (AnA) was put in a round bottom flask and bubbled with nitrogen or argon gas for at least 30 min. A piece of the H-terminated silicon substrate was then immersed in the solution and allowed to react with VA or AnA for about 12 h under reflux at about 150° C. in an oil bath. During the reaction, the solution was also purged with nitrogen (or argon) to eliminate dissolved oxygen and to prevent the substrate from being oxidized. After the reaction, the substrate derivatized with VA or AnA was rinsed with dichloromethane, acetonitrile and methanol, and dried under a stream of nitrogen gas. The derivatization of the H-terminated surface with anthracene moieties as described in Example 3 is illustrated in FIG. 6.

Example 4

Derivatization of H-Terminated Silicon Surface with Both the Anthracene and Ferrocene Moieties A 10 mmol mesitylene solution of anthracene (VA or AnA) and ferrocene (VFc or FcA) in 1:1 ratio was put in a round bottom flask and bubbled with nitrogen or argon gas for at least 30 min. A piece of the H-terminated silicon substrate was then immersed in the solution and allowed to react with the anthracene and ferrocene mixtures for about 12 h under reflux at 150° C. in oil bath. During the reaction, the solution was also purged with nitrogen (or argon) to eliminate dissolved oxygen and to prevent the substrate from being oxidized. After the reaction, the derivatized substrate was rinsed with dichloromethane, acetonitrile and methanol, and dried under a stream of nitrogen gas. FIG. 7 illustrates a reaction in which the silicon surface derivatized with both the anthracene and ferrocene using VFc and VA.

Example 5

Figure 8:
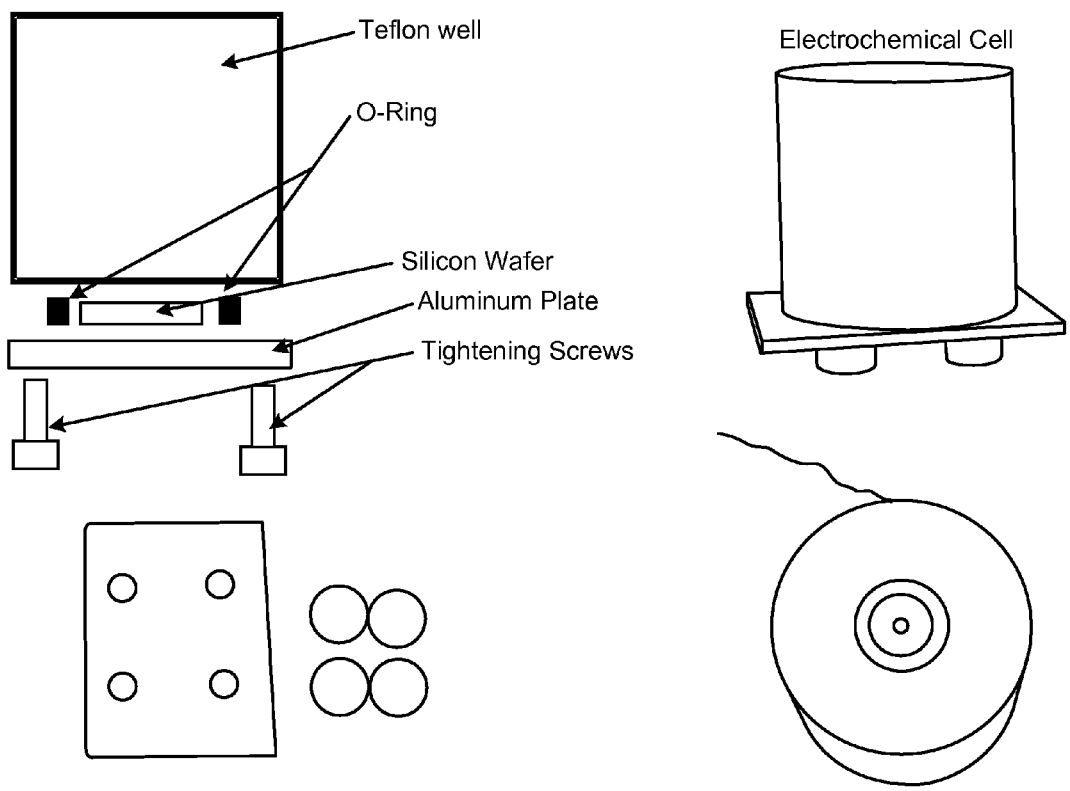
FIG. 8 depicts a schematic diagram and picture of an exemplary electrochemical cell.

Electrochemical Measurements of the Derivatized Silicon Wafers in Different pH Solutions Square wave (SW) voltammetry was carried out for the derivatized silicon wafers in a specially designed electrochemical cell as shown in FIG. 8. The electrochemical measurements were performed using a standard three-electrode configuration. In these experiments, the derivatized silicon wafers were used as the working electrode, and was exposed to different pH solutions (about 10 mL) in the electrochemical cell. SWV were performed with a frequency of 10 Hz, a step potential of 2 mV and an amplitude of 25 mV.

Figure 9:
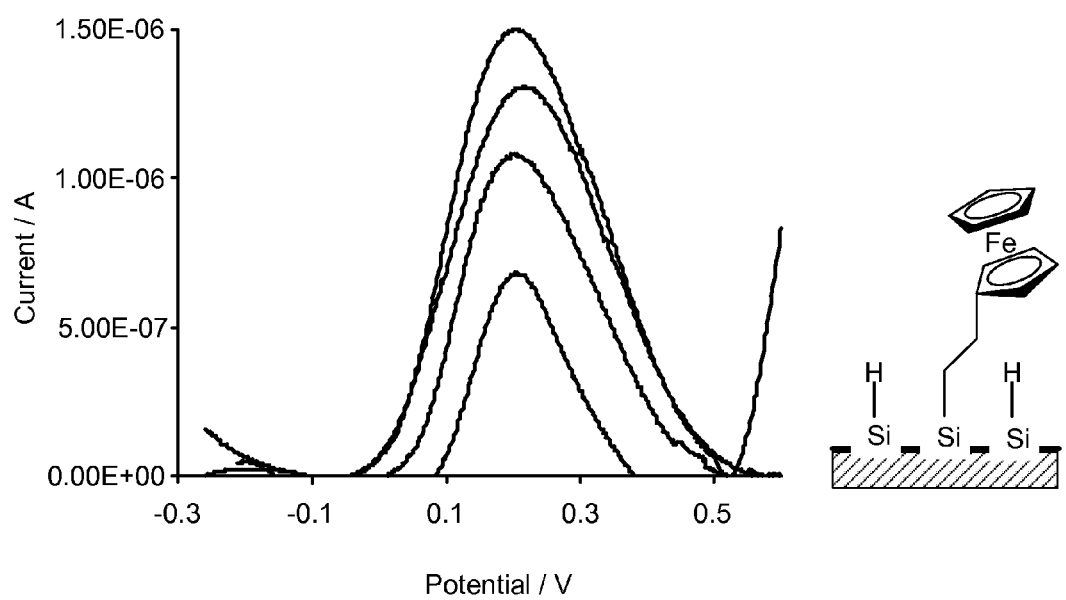
FIG. 9 depicts SW voltammograms showing the effect of pH on VFc derivatized silicon sample at pH solution of 1.23, 4.61, 7.33 and 9.33.

The amperometric response of the anthracene or ferrocene derivatized silicon substrate at different pH solutions was studied using SWV. SWV was used as the electrochemical probe of the system because it produces a well-defined voltammetric peak in a single sweep. The corresponding SW voltammograms recorded using a derivatized ferrocene electrode at different pH solutions from pH 1.23 to 9.33 are shown in FIG. 9. These voltammograms show that as the pH values increase, the peak potential of the ferrocene peaks remain at the same peak potential. These results show that ferrocene is a pH insensitive molecule which can act as an internal reference material.

Figure 10:
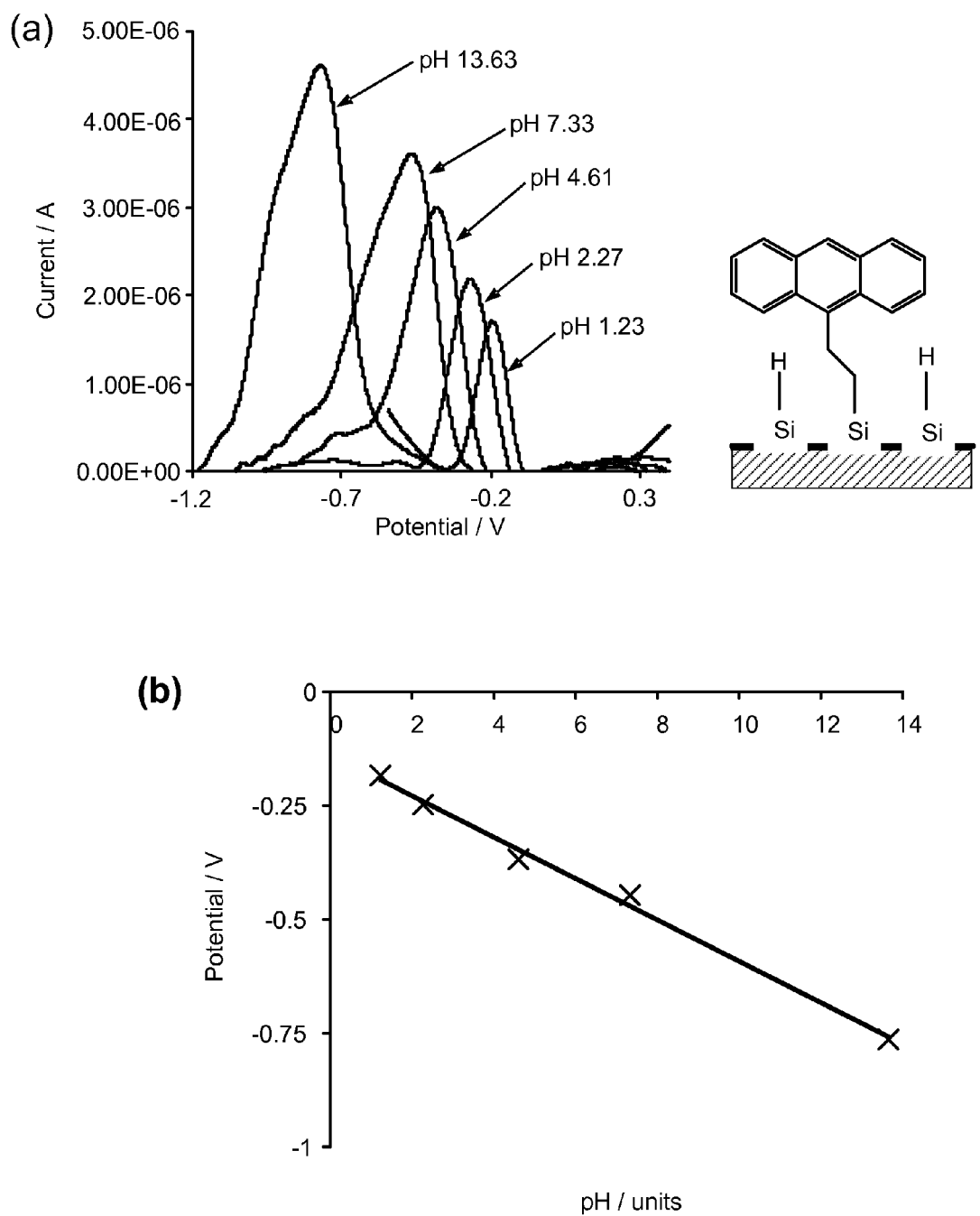
FIG. 10(a) depicts SW voltammograms showing the effect of pH on VA derivatized silicon sample at pH solutions of 1.23, 4.61, 7.33 and 9.33.
FIG. 10(b) A plot of peak potential against pH using the VA derivatized silicon sample.

The corresponding SW voltammograms recorded using a derivatized anthracene electrode at different pH solutions, from pH 1.23 to 13.63, are shown in FIG. 10(a). These voltammograms show that as the pH value increases, the peak potential attributed to the anthracene shifts to a more negative potential. The corresponding plot of the peak potential against different pH is given in FIG. 10(b). The plot reveals a linear response from pH 1 to pH 14 with a corresponding gradient of ca 55.1 mV per pH unit. The ability of anthracene compounds to act as pH sensitive molecule is thus demonstrated.

Figure 11:
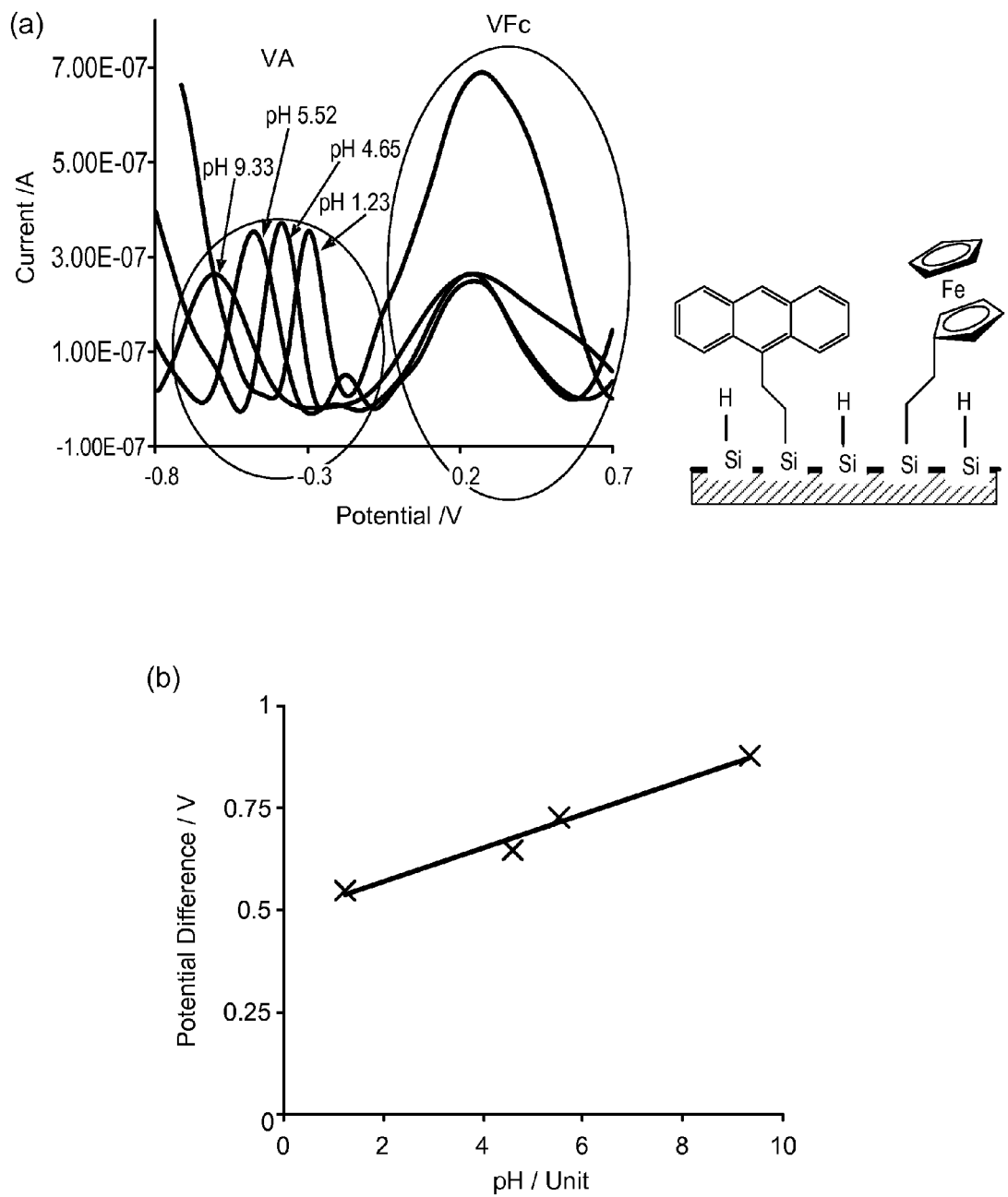
FIG. 11 depicts: (a) SW voltammograms showing the effect of pH on VA+VFc derivatized silicon sample at pH solutions of 1.23, 4.65, 5.52 and 9.52; and (b) a plot of peak potential difference against pH using the VA+VFc derivatized silicon sample.

The corresponding SW voltammograms recorded using a derivatized ferrocene+anthracene electrode at different pH solutions, from pH 1.23 to 9.33, are shown in FIG. 11(a). These voltammograms illustrate that as the pH values increase, the ferrocene peak remains at the same peak potential while the anthracene peak shifts to a more negative potential. The corresponding plot of the difference between the two peak potentials versus pH is shown in FIG. 11(b). The plot reveals a linear response from pH 1 to pH 9.33 with a corresponding gradient of ca 45.1 mV per pH unit.

Example 6

Heat Stability

A SW voltammogram was recorded for the silicon wafer derivatized with both VA and FcA moieties at room temperature in pH 6.52 buffer. The derivatized silicon sample was then autoclaved in the Consolidated Stills & Sterilizers for 40 min, and a SW voltammogram was recorded in pH 6.52 buffer after the autoclave. Next, the same sample was autoclaved again under the same condition for up to 10 times, with a SW voltammogram recorded in pH 6.52 buffer after each autoclave.

Figure 12:
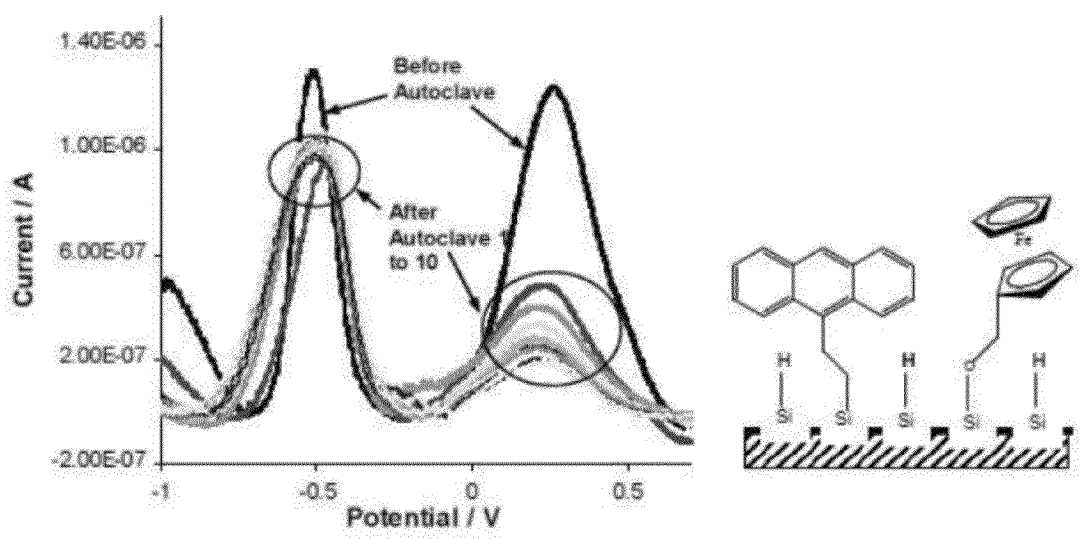
FIG. 12 depicts SW voltammograms showing the effect of 10 autoclave cycles on FcA+VA derivatized silicon sample. The electrochemical measurements were conducted at ph 6.52 buffer prior to autoclave and after autoclave.

The heat stability testing of the pH sensor was performed using a FcA+VA derivatized silicon sample. The resultant voltammograms are shown in FIG. 12. Although a decrease in both the ferrocene and anthracene currents were observed after the first autoclave, both the peak currents remain relatively stable though subsequent cycles of autoclaving; in fact the peaks remain stable for ten cycles, showing that the sensor can withstand repeated heat sterilization.

Example 7

Fouling Test

Four SW voltammograms were recorded for the four separate silicon wafers derivatized with FcA and AnA moieties at room temperature in pH 6.52 buffer. These derivatized samples were then autoclaved in the Consolidated Stills & Sterilizers for 20 min and were immersed in a 5 mL cell culture fermentation for six days. Then these samples were taken out of the cell culture medium, and SW voltammograms were recorded in pH 6.52 buffer again. SW voltammetry was also carried out in the cell culture medium, using the same silicon wafers.

Figure 13:
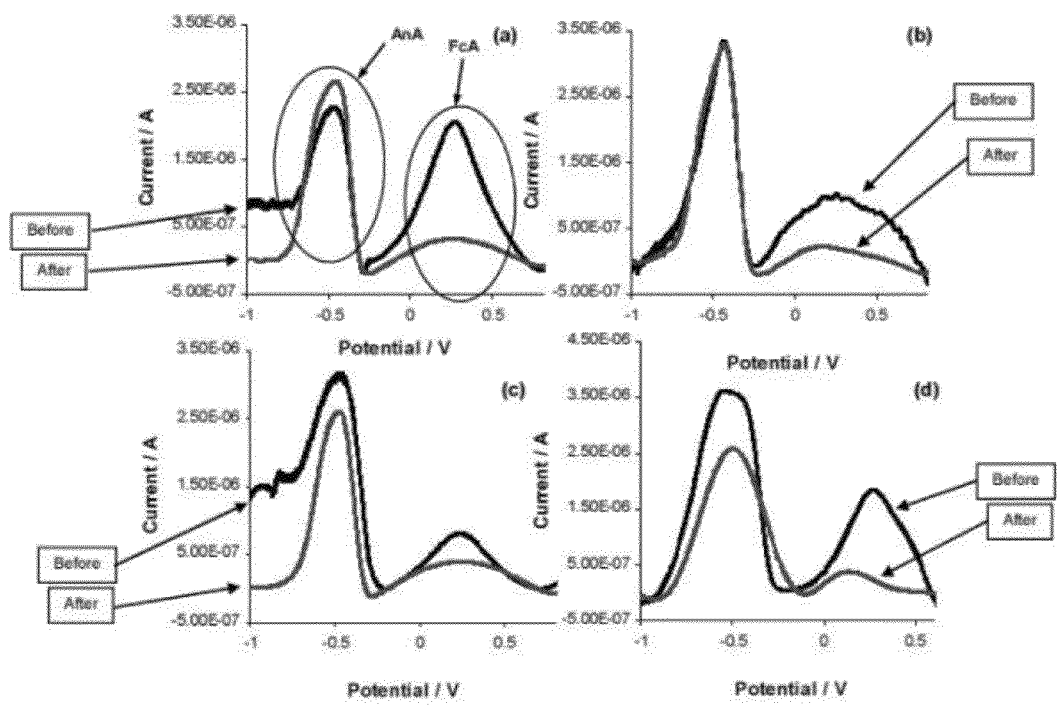
FIG. 13 depicts SW voltammograms showing the effect of fouling on FcA+AnA derivatized silicon samples. The electrochemical measurements were conducted at pH 6.52 buffer before and after six days exposure in the cell culture at four different FcA+AnA derivatized silicon samples (a), (b), (c) and (d).
Figure 14:
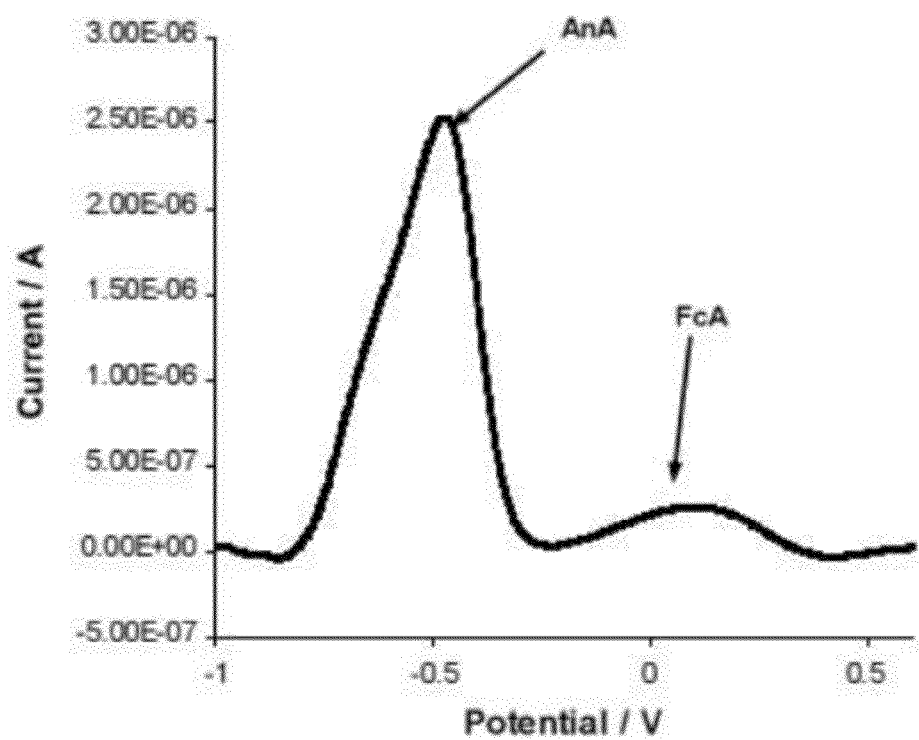
FIG. 14 depicts an SW voltammogram obtained at FcA+AnA derivatized silicon sample in cell culture medium after sterilization and 6 days exposure.

The fouling testing of the pH sensor was performed using five derivatized silicon samples. The resultant voltammograms were shown in FIG. 13. In all cases, the anthracene peaks remain stable with after six days exposure. The ferrocene peaks decrease after exposure, but the ferrocene peaks are still identifiable. These findings demonstrate that the pH sensors are still in good working order after six days exposure to the cell culture environment, demonstrating that the ability of the derivatized sensor to resist fouling. A control sensor was incubated for 6 days in culture fluid without cells or secreted proteins. This sensor's voltammogram exhibited a similar profile to the four that had been incubated in the actual cell fermentation environment, (FIG. 14) suggesting that any loss of signal amplitude was not a function of cellular debris deposition.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 8

Stability of the Anthracene and Ferrocene Derivatized Si Surfaces

The stability testing of the Ac+Fc derivatized silicon surface was conducted for 22 days under continuous electrochemical measurement using PGSTAT12 autolab potentiostat in pH 4.65 buffer medium, scanning from −0.8 V to 0.8 V vs. Ag. The Ac peak remained as a well-defined peak with a full width half maximum (FWHM) of ~60 mV throughout the course of the experiments, while the Fc peaks became less-defined with time, i.e. grew broader. Although the Fc peaks became broader, they are still identifiable and can be used as a reference. These findings demonstrate that the two-component derivatized silicon surface are still in good working order after 22 days continuous operation in pH 4.65 buffer medium, demonstrating the long term stability of the derivatized surface in the buffer medium.

Figure 15:
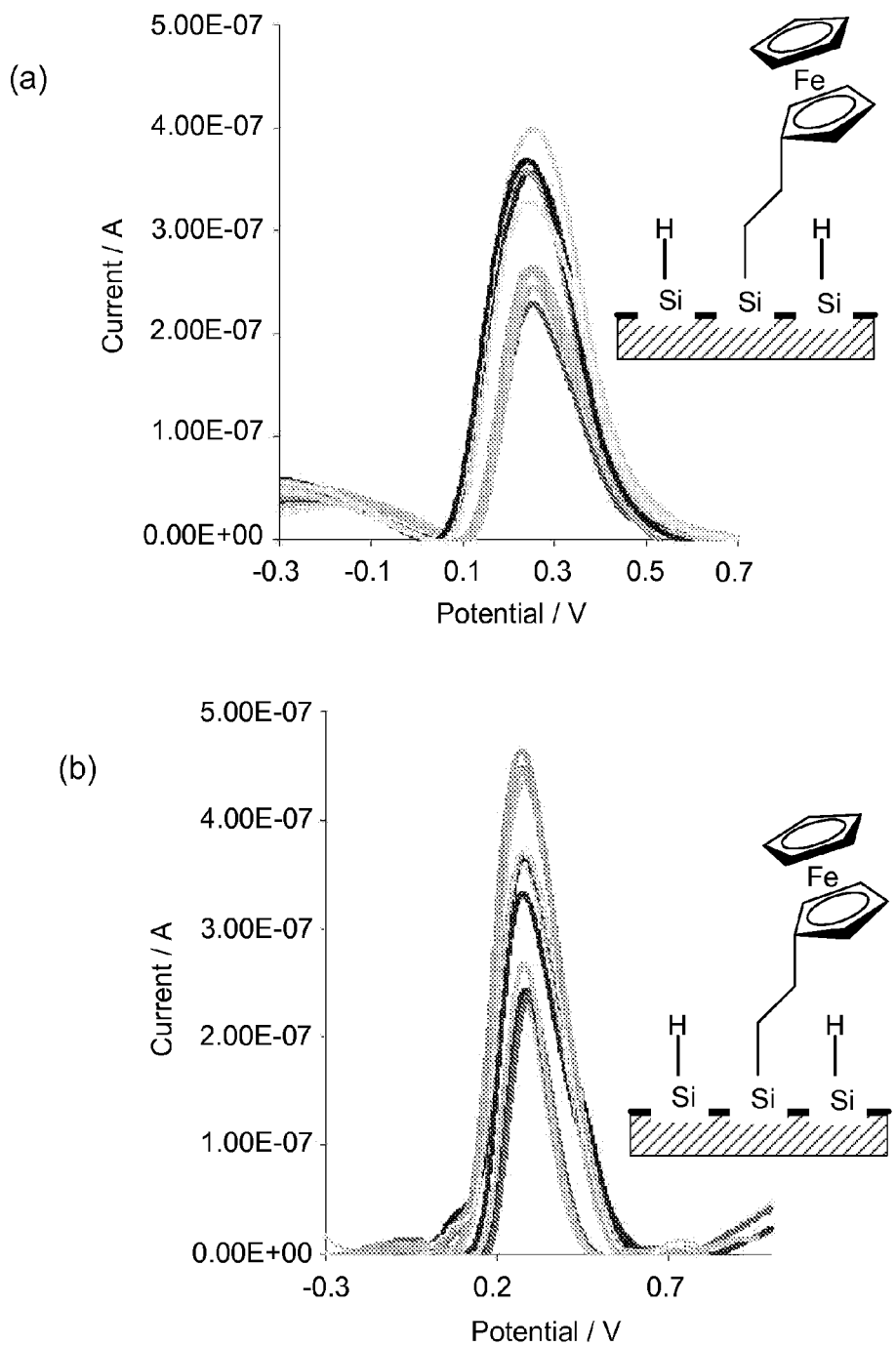
FIG. 15(a) depicts SW voltammetric responses FcA on Si(100, N-type, 1-5 mΩ cm) in pH 7.33 buffer medium, showing every $50^{th}$ scan of the 2,500 consecutive runs.
FIG. 15(b) depicts voltammetric responses of VFc on Si(111, N-type, 0.02-0.05Ω cm in pH 7.33 buffer medium, showing every $50^{th}$ scan of the 2,500 consecutive runs.

In general, the Fc peaks are most well-defined and stable when the Fc molecules were derivatized onto a heavily doped silicon substrate. FIG. 15($a$) depicts SW voltammetric responses FcA on Si(100, N-type, 1-5 mΩ cm) in pH 7.33 buffer medium, showing every $50^{th}$ scan of the 2,500 consecutive runs; FIG. 15($b$) depicts voltammetric responses of VFc on Si(111, N-type, 0.02-0.05Ω cm in pH 7.33 buffer medium, showing every $50^{th}$ scan of the 2,500 consecutive runs. In some cases, both VFc and FcA moieties behave better on an n-type substrate than a p-type substrate in terms of the size of the peak current produced. The Fc derivatized silicon surfaces were all pH insensitive, i.e. the Fc peak does not shift upon exposure to different pH environments.

Example 9

Temperature Variation

The Nernst equation provides a theoretical framework for evaluating the temperature dependence of redox active species. It predicts that the slope of the peak potential against pH plot will increase as the temperature increases:

$$E_p = E_f^0 - \frac{2.3RTm}{nF}\text{pH} \qquad \text{Eq. 1}$$

Where $E_p$ is the peak potential (V), $E_f^0$ is the standard electrode potential (V), R is the universal gas constant (J K$^{-1}$ mol$^{-1}$), T is the absolute temperature (K), F is the Faraday constant (C mol$^{-1}$), m and n are the number of protons and electrons involved in the redox reaction, respectively. In the case of anthracene, the redox process for such molecules in the aqueous solution involves the participation of 2 electrons and 2 protons, thus m=n=2.

Figure 16:
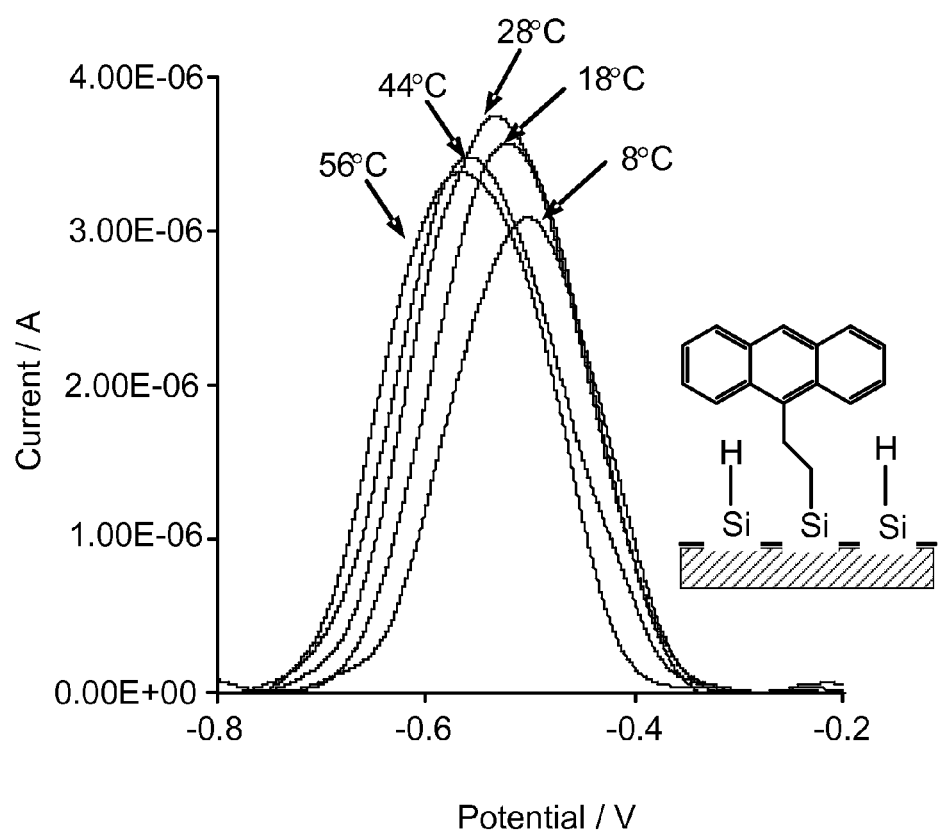
FIG. 16 depicts the SW voltammetric response of Ac derivatized silicon surface at various temperatures (8, 17, 28 44, 56° C.) in pH 7.33 buffer medium.

SW voltammograms were recorded for three pH solutions at pH 4.65, 7.33 and 9.35. FIG. 16 shows the overlaid SW voltammograms of Ac derivatized silicon over the temperature range of 8 to 56° C. in pH 7.33 buffer medium. Similar responses were obtained at pH 4.65 and pH 9.35. There is a shift of the peak potential to more negative values with increasing temperature which may be attributed in part to a combination of changes in the reference couple, the temperature dependence of the formal potential ($E_f^0$), and the temperature term in Eq. 1. Analysis of the slope of the peak potential as a function of pH obtained experimentally at each temperature is tabulated in Table 1, which illustrates that the slope of pH against peak potential plot varies with temperature. The theoretical slope as predicted by the Nernst equation as seen in Eq 1. is also listed in Table 1 for comparison. As can be seen, the variation of the gradient of peak potential with pH is not Nernstian and indeed is relatively insensitive of temperature varying by about 2 mV/pH unit over a temperature range of ~50° C. This dependence can be compared to a 10 mV/pH shift that can be observed for a glass electrode. This small shift with temperature is beneficial in that it not only demonstrates that these Ac derivatized silicon wafers may be used as pH sensors at elevated temperatures, but also that they are not greatly affected by changes in temperature.

TABLE 1

A comparison of the theoretically predicted slope and experimentally obtained slope of the plot of pH against Ac peak potential for a range of temperatures.

| | T (° C.) | | | | |
|---|---|---|---|---|---|
| | 8 | 17 | 28 | 44 | 56 |
| T (K) | 281 | 290 | 301 | 317 | 329 |
| Theoretical (mV/pH) | 55.7 | 57.5 | 59.7 | 62.8 | 65.2 |
| Experimental (mV/pH) | 55.0 | 55.5 | 56 | 56.3 | 57.0 |

Example 10

Stability During Active Measurement in Cell Culture Medium

A fouling testing was carried out using anthracene derivatized silicon (100) wafer in the incubator (under controlled temperature of 37° C. and $CO_2$ content of 5%) with continuous electrochemical measurements in cell culture (LP VA) medium for 7 days using a three-electrode setup connected to an μ autolab type III potentiostat. The three-electrode setup (in an electrochemical cell) was autoclaved in the Consolidated Stills & Sterilizers autoclave for 40 min prior to adding 5 mL of the cell culture medium to the autoclaved setup. The electrochemical cell containing the medium was then transferred to the incubator, where continuous electrochemical measurements were performed.

Figure 18:
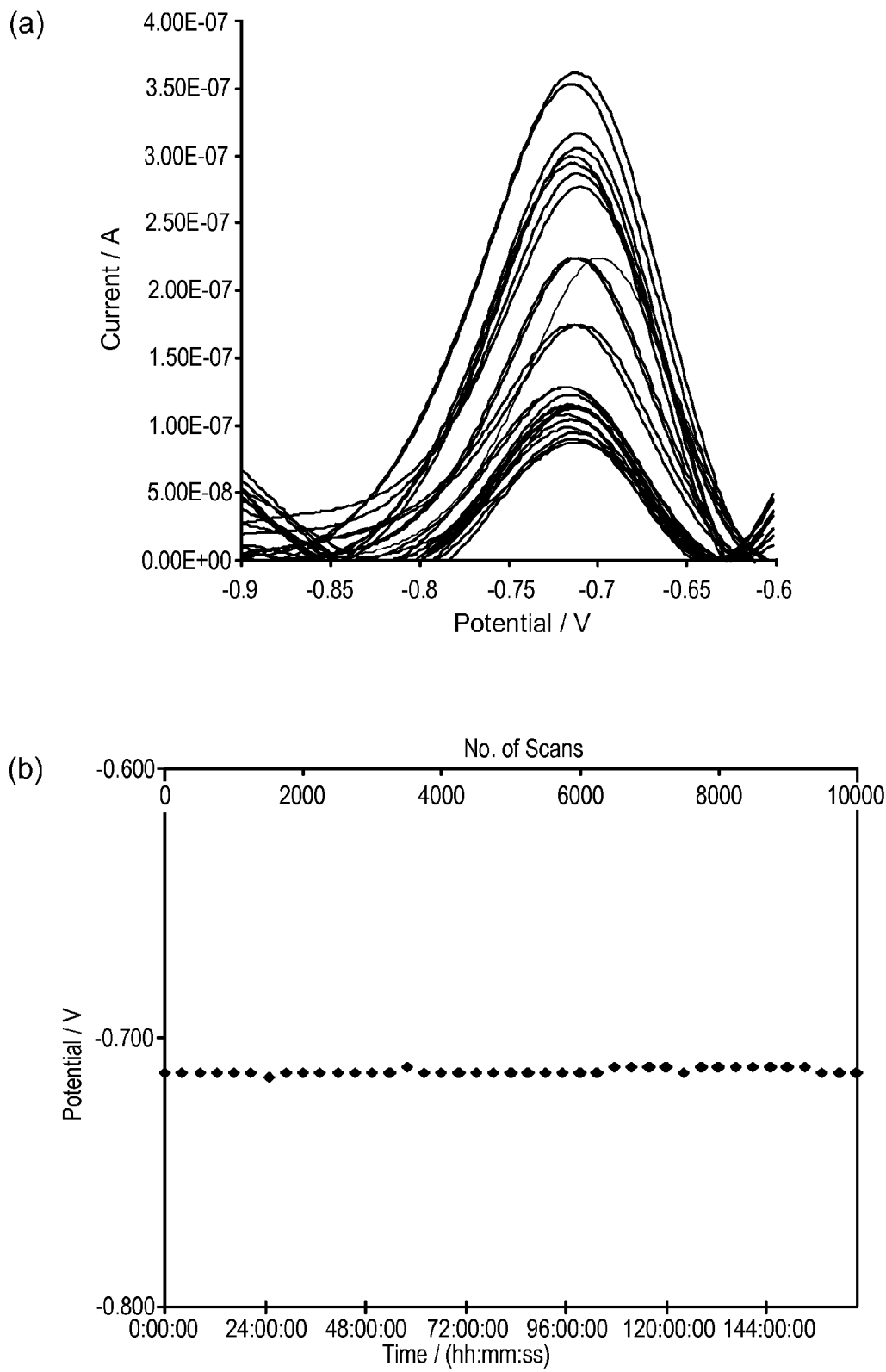
FIG. 18(a) depicts voltammograms taken on an anthracene derivatized silicon sensor over the 7 day period in cell culture medium (every $250^{th}$ scan of the 10,000 consecutive runs).
FIG. 18(b) depicts a plot of the anthracene peak potential over the 7 day time period

Voltammograms were taken repeatedly over 7 days resulting in 10,000 consecutive voltammograms. FIG. 18(a) shows voltammograms taken over the 7 day period (every $250^{th}$ scan of the 10,000 consecutive runs). The anthracene peak was observed at ~−0.71V vs. Ag and remained consistent throughout the 7 days of in-situ electrochemical measurements in the cell culture medium. A plot of the anthracene peak potential over the 7 day time period is shown in FIG. 18(b). These findings demonstrate that the anthracene derivatized silicon is still in good working order and that the peak potential remains consistent while the sensor is actively sensing the solution for 7 days.

What is claimed is:

1. A pH sensor, comprising:
 a non-metallic solid state electrode having a surface having immobilized thereon a redox-active moiety, wherein the redox-active moiety exhibits an oxidation potential and/or a reduction potential that is sensitive to the presence of hydrogen ion,
 wherein the redox-active moiety is immobilized on the surface of the solid state electrode through a carbon covalent bond, and
 wherein said pH sensor has a sensitivity of at least about 45.1 mV per pH unit.

2. The pH sensor of claim 1, further comprising an additional redox-active moiety having an oxidation potential and/or reduction potential that is insensitive to the presence of hydrogen ion, wherein said additional redox-active moiety is immobilized on i) said surface or ii) a surface of an additional electrode.

3. The pH sensor of claim 1, wherein said non-metallic solid state electrode is formed of silicon.

4. The pH sensor of claim 1, wherein the pH sensor has an accuracy to within about 0.5 pH units or less.

5. The pH sensor of claim 1, wherein the non-metallic solid state electrode is chemically doped.

6. The pH sensor of claim 5, wherein the non-metallic solid state electrode is chemically doped p-type.

7. A pH sensor, comprising:
 a first non-metallic working electrode having a surface having immobilized thereon a first redox-active moiety, wherein the first redox-active moiety exhibits an oxidation potential and/or a reduction potential that is sensitive to the presence of hydrogen ion; and
 a second non-metallic working electrode electrically isolated from said first working electrode, said second working electrode having a surface having immobilized thereon a second redox-active moiety, wherein the second redox-active moiety exhibits an oxidation potential and/or a reduction potential that is insensitive to the presence of hydrogen ion,
 wherein said pH sensor has an accuracy to within about 1 pH unit or less while in use or storage for about ten hours or more.

8. The pH sensor of claim 7, wherein said pH sensor has an accuracy to within about 0.5 pH units or less.

9. The pH sensor of claim 7, wherein said pH sensor has an accuracy to within about 0.02 pH units or less.

10. The pH sensor of claim 7, wherein said first non-metallic working electrode is formed of silicon.

11. The pH sensor of claim 7, wherein the pH sensor has a sensitivity of at least about 45.1 mV per pH unit.

12. The pH sensor of claim 7, wherein the pH sensor is accurate at measuring the concentration of hydrogen ion to about 10% or less while in use or storage for about ten hours or more.

13. The pH sensor of claim 7, wherein the pH sensor is accurate at measuring the concentration of hydrogen ion to about 1% or less while in use or storage for about ten hours or more.

14. The pH sensor of claim 7, wherein the first redox-active moiety is immobilized on the surface of the first non-metallic working electrode by a carbon covalent bond between said redox-active moiety and said surface.

15. A calibration-free sensor, comprising:
 a non-metallic electrode having a surface having immobilized thereon a redox-active moiety exhibiting an oxidation potential and/or a reduction potential that is sensitive to the presence of hydrogen ion; and
 a microprocessor programmed to measure the concentration of said hydrogen ion at an accuracy within about 50% or less while in use or storage for about ten hours or more without calibration.

16. The calibration-free sensor of claim 15, further comprising an additional redox-active moiety having an oxidation potential and/or reduction potential that is insensitive to the presence of said hydrogen ion, wherein said additional redox-active moiety is immobilized on i) said surface or ii) a surface of an additional electrode.

17. The calibration-free sensor of claim 15, wherein the sensor is accurate at measuring the concentration of said hydrogen ion to about 10% or less when in use or storage for about ten hours or more.

18. The calibration-free sensor of claim 15, wherein the sensor is accurate at measuring the concentration of said hydrogen ion to about 2% or less when in use or storage for about ten hours or more.

19. The calibration-free sensor of claim 15, wherein the sensor is accurate at measuring the concentration of said hydrogen ion to about 1% or less when in use or storage for about ten hours or more.

20. The calibration-free sensor of claim 15, wherein said non-metallic electrode is formed of silicon.

21. The calibration-free sensor of claim 15, wherein the sensor has a sensitivity of at least about 45.1 mV per pH unit.

22. The calibration-free sensor of claim 15, wherein the redox-active moiety is immobilized on the surface by a carbon covalent bond between said redox-active moiety and said surface.

23. A system, comprising:
a sensor comprising a non-metallic solid state electrode having a surface having immobilized thereon a redox-active moiety exhibiting an oxidation potential and/or a reduction potential that is sensitive to the presence of an hydrogen ion; and
a power supply that provides power to said sensor to sense said hydrogen ion, said power supply comprising a battery,
wherein the sensor is disposable or single-use.

24. The system of claim 23, further comprising an additional redox-active moiety having an oxidation potential and/or reduction potential that is insensitive to the presence of said hydrogen ion, wherein said additional redox-active moiety is immobilized on i) said surface or ii) a surface of an additional electrode that is electrically isolated from said solid state electrode.

25. The system of claim 23, wherein said non-metallic solid state electrode is formed of silicon.

26. The system of claim 23, wherein said power supply is a disposable, chemically-based battery.

27. The system of claim 23, wherein said power supply is an encapsulated module removable from said disposable or single-use sensor.

28. The system of claim 23, wherein the redox-active moiety is immobilized on the surface by a carbon covalent bond between said redox-active moiety and said surface.

29. The system of claim 23, wherein said non-metallic solid state electrode is substantially planar.

30. The system of claim 23, wherein the sensor is accurate at measuring the concentration of said hydrogen ion to about 1% or less when in use or storage for about ten hours or more.

* * * * *